United States Patent
Ide

(10) Patent No.: US 7,858,030 B2
(45) Date of Patent: Dec. 28, 2010

(54) ARTIFICIAL LIPID BILAYER MEMBRANE FORMATION DEVICE, ARTIFICIAL LIPID BILAYER MEMBRANE FORMATION METHOD, AND USAGE THEREOF

(75) Inventor: Toru Ide, Toyonaka (JP)

(73) Assignee: Japan Science and Technology Agency, Saitama (JP)

( * ) Notice: Subject to any disclaimer, the term of this patent is extended or adjusted under 35 U.S.C. 154(b) by 1200 days.

(21) Appl. No.: 10/572,205

(22) PCT Filed: Sep. 17, 2004

(86) PCT No.: PCT/JP2004/013680

§ 371 (c)(1),
(2), (4) Date: Jun. 26, 2006

(87) PCT Pub. No.: WO2005/029056

PCT Pub. Date: Mar. 31, 2005

(65) Prior Publication Data

US 2006/0251709 A1    Nov. 9, 2006

(30) Foreign Application Priority Data

Sep. 19, 2003  (JP)  .............................. 2003-328651

(51) Int. Cl.
*G01N 21/00* (2006.01)
*G01N 31/22* (2006.01)
*A61K 9/127* (2006.01)

(52) U.S. Cl. .......................... 422/58; 424/450; 436/166

(58) Field of Classification Search ......... 427/384–397; 436/151, 178, 63, 531, 501, 806, 179, 166; 204/403, 153.12, 252, 418, 403.01–403.06; 422/82.01, 58; 435/4, 7, 817; 424/450; 607/71, 607/76; 205/778, 777.5; 324/444, 439, 71.1, 324/71.5, 450, 464; 210/321.6, 257.2, 500.27, 210/638

See application file for complete search history.

(56) References Cited

U.S. PATENT DOCUMENTS

| | | | | |
|---|---|---|---|---|
| 3,799,743 | A | * | 3/1974 | Alexander et al. ........ 422/82.02 |
| H000201 | H | * | 1/1987 | Yager ......................... 436/151 |
| 4,959,355 | A | * | 9/1990 | Fischbarg et al. ............. 514/23 |

(Continued)

OTHER PUBLICATIONS

Benz et al., Effects of hydrostatic pressure on lipid bilayer membranes, Jul. 1986, J. Biophysical Society, pp. 99-107.*

(Continued)

*Primary Examiner*—Tony G Soohoo
*Assistant Examiner*—David C Mellon
(74) *Attorney, Agent, or Firm*—Harness, Dickey & Pierce, P.L.C.

(57) ABSTRACT

An artificial lipid bilayer membrane formation device is disclosed. It includes: an upper solution chamber whose bottom has a small hole; a lower solution chamber having a support layer; and lipid solution exclusion device. Lipid solution is applied to the small hole, and the lipid solution exclusion device excludes surplus lipid solution without changing a hydraulic pressure so that the lipid solution is in contact with the support layer, thereby forming an artificial lipid bilayer membrane on the small hole.

5 Claims, 16 Drawing Sheets (a)

U.S. PATENT DOCUMENTS

| | | | | |
|---|---|---|---|---|
| 5,185,154 | A | * | 2/1993 | Lasic et al. ............... 424/450 |
| 5,288,517 | A | * | 2/1994 | Kanno et al. ............... 427/244 |
| 5,368,712 | A | * | 11/1994 | Tomich et al. ......... 204/403.06 |
| 5,378,342 | A | * | 1/1995 | Ikematsu et al. ....... 204/403.06 |
| 5,411,730 | A | * | 5/1995 | Kirpotin et al. .......... 424/9.322 |
| 5,443,955 | A | * | 8/1995 | Cornell et al. ............. 435/7.21 |
| 5,503,744 | A | * | 4/1996 | Ikematsu et al. ....... 204/403.06 |
| 5,665,380 | A | * | 9/1997 | Wallach et al. ............. 424/450 |
| 5,688,752 | A | * | 11/1997 | Turner ....................... 510/159 |
| 5,741,409 | A | * | 4/1998 | Raguse et al. ......... 204/403.08 |
| 5,783,054 | A | * | 7/1998 | Raguse et al. ......... 204/403.08 |
| 5,827,533 | A | * | 10/1998 | Needham .................... 424/450 |
| 5,879,878 | A | * | 3/1999 | Raguse et al. .................. 435/4 |
| 5,922,594 | A | * | 7/1999 | Lofås ..................... 435/287.1 |
| 6,291,155 | B1 | * | 9/2001 | Raguse et al. .................. 435/4 |
| 6,432,629 | B1 | * | 8/2002 | Raguse et al. .................. 435/4 |
| 6,451,543 | B1 | * | 9/2002 | Kochendoerfer et al. ..... 435/7.1 |
| 6,565,889 | B2 | * | 5/2003 | Zasadzinski et al. ........ 424/490 |
| 6,689,083 | B1 | * | 2/2004 | Gelfand et al. ............. 604/5.04 |
| 6,726,925 | B1 | * | 4/2004 | Needham .................... 424/450 |
| 6,863,833 | B1 | * | 3/2005 | Bloom et al. ................... 216/2 |
| 2002/0063067 | A1 | * | 5/2002 | Bech et al. .................. 205/775 |
| 2003/0052002 | A1 | * | 3/2003 | Vogel et al. ............ 204/403.01 |
| 2003/0054027 | A1 | * | 3/2003 | Unger ........................ 424/450 |
| 2003/0062657 | A1 | | 4/2003 | Parameswaran et al. |
| 2003/0098248 | A1 | * | 5/2003 | Vogel et al. ............... 205/777.5 |
| 2004/0110307 | A1 | * | 6/2004 | Karlsson et al. ............. 436/518 |
| 2004/0120854 | A1 | * | 6/2004 | Heath et al. .................... 422/57 |
| 2008/0089927 | A1 | * | 4/2008 | Malinin ....................... 424/450 |
| 2009/0143308 | A1 | * | 6/2009 | Monk et al. .................... 514/16 |
| 2010/0196203 | A1 | * | 8/2010 | Sanghera et al. ........... 422/68.1 |

OTHER PUBLICATIONS

Tien et al., The lipid bilayer concept and its experimental realization: from soap bubbles, kitchen sink, to bilayer lipid membranes, 2001, Elsevior, Journal of Membrane Science, pp. 83-117.*

Tien et al., Planar lipid bilayers (BLMs) and their applications, 2003, Elsevior, pp. 381-382,450-454,807-819,825-829.*

Suzuki et al., Formation process of planar lipid bilayer observed by confocal microscopy, May 15, 2005, pp. 272-275.*

Leonenko et al., Supported planar bilayer formation by vesicle fusion: the interaction of phospholipid vesicles with surfaces and the effect of gramicidin on bilayer properties using atomic force microscopy, 2000, Elsever, Biochimica et biophysica acta, pp. 131-147.*

Charras et al., Estimating the sensitivity of mechanosensitive ion channels to membrane strain and tension, Oct. 2004, Biophysical Journal, vol. 87, pp. 2870-2884.*

Batishchev et al., Alkylated glass partition allows formation of solvent-free lipid bilayer by montal-mueller technique, 2008, Elsevier, Bioelectrochemistry, pp. 22-25.*

Toru Ide et al., Seirigaku Jikken Koza "1 Bunshi Seirigaku", "Tan'itsu Channel no Denki Kogakuteki Doji Keisoku", Nihon Seirishi, vol. 65, No. 9, 283 to 290 (particularly, p. 287 (5) to (7), Fig. 3), Sep. 1, 2003.

Toru Ide et al., "An Artificial Lipid Bilayer Formed on an Agarose-Coated Glass for Simultaneous Electrical and Optical Measurement of Single Ion Channels", Biochemical and Biophysical Research Communications, vol. 265 pp. 595-599, 1999.

A.G. MacDonald et al., "Combined Spectroscopic and Electrical Recording Techniques in Membrane Reserch: Prospects for Single Channel Studies", Prog. Biophys. Molec. Biol., vol. 63, pp. 1-29, 1995.

Toshiro Hamamoto, "Heimen Rin Shishitsu Nijusomaku O Tsukatta Ion Channel no Sokutei", Cell Technology, vol. 7, No. 1, 87 to 96 (particularly, p. 92, Fig. 6, Hakenuriho, line 10), 1988.

Naritoshi Oiki, "Planar Bilayer Method for Studying Channel," New Patch Clamping Experiment Technique, 2001, pp. 208-215.

Toru Ide et al., "Physiological Experiment Lectures 'Monomolecular Physiology' Electrical/optical simultaneous measurement of single channel," Japan Physiological Magazine, vol. 65, No. 9, 2003, pp. 283-290.

Toshiro Hamamoto et al., "Measurement of Ion Channel Using Planar Phospholipid Bilayer Membrane," Cell Technology, vol. 7, No. 1, 1988, pp. 87-96.

Toru Ide et al., "Development of an Experimental Apparatus for Simultaneous Observation of Optical and Electrical Signals from Single Ion Channels," Single Molecules 3 (2002)1, pp. 33-42.

Takeuchi Yuko et al., "Simultaneous observation of optical and electrical signals from single ion channels," Neuroscience Research Supplement, Elsevier, Shannon, IR LNKD-DOI: 10.1016/S0168-0102(03)00075-0, vol. 45, No. 1 (suppl. 26), Jul. 9, 2002, p. S15, XP00913577, retrieved on Mar. 26, 2003, p. 430-431, abstract only.

Search Report for corresponding European Application No. 04773299.5 dated Jul. 30, 2010.

* cited by examiner (a)

(b)

(a)

(b)

(c)

(a)

(b)

(a)

(b)

(c)

(a)

pCa 3    P₀ > 0.95

(b)

pCa 8    P₀ < 0.05

Membrane Potential=+60mV $\gamma \approx 220 \text{ pS}$ (a)

ARTIFICIAL LIPID BILAYER MEMBRANE FORMATION DEVICE, ARTIFICIAL LIPID BILAYER MEMBRANE FORMATION METHOD, AND USAGE THEREOF

TECHNICAL FIELD

The present invention relates to an artificial lipid bilayer membrane formation device, an artificial lipid bilayer membrane formation method, and usage thereof. Specifically, the present invention relates to (i) a device and (ii) a method for forming an artificial lipid bilayer membrane favorably used in a planar lipid bilayer method adopted to detect a minute current via a membrane protein, peptide, and the like for example, and (iii) an example of typical usage thereof.

BACKGROUND ART

A lipid bilayer membrane is a basic structure of a biological membrane, and is found in a biological membrane of every living organism. In most of biological membranes, various membrane proteins are provided in the lipid bilayer membrane, and the membrane protein is involved in (i) transportation of substances such as various types of ion, sugar, amino acid, nucleotide, and the like, (ii) transmission of signals, or (iii) synthesis of lipid.

In this way, the biological membrane is a place for exhibiting vital functions and plays various important roles such as recognition of external information, transmission of the information into the membrane, conversion of the substance, transportation of the substance, and the like. Further, in case of applying functions of the biological membrane, various industrial applicability can be found. Thus, it is extremely important to produce an artificial membrane as a biological membrane model.

As the artificial membrane serving as the biological membrane model, various membranes such as a polymer cast membrane, a Langmuir-Blodigett (LB) membrane, and the like are used, but an artificial lipid bilayer membrane is most similar to the biological membrane. The artificial lipid bilayer membrane is a thin membrane in which amphipathic molecules are aligned so that alkyl chains of hydrophobic portions of the amphipathic molecules internally face each other. For example, the artificial lipid bilayer membrane is applied to measurement of an ion current of an ion channel and a similar use.

Incidentally, as a method for forming the artificial lipid bilayer membrane, the planar lipid bilayer method is known. As a method for measuring an ion current of a single ion channel, a patch-clamp method is adopted. However, in order to more deeply study correlation of structural functions of the channel, it is necessary to use a simple rearrangement system in carrying out an experiment. An artificial lipid bilayer membrane formation method adopted in this case is the planar lipid bilayer method.

In the planar lipid bilayer method, a minimum simple system including ion, water, an artificial lipid bilayer membrane, and an ion channel is used so as to study a basic structure of the ion channel and detail correlation of structural functions thereof (Non-Patent Document 1).

The following specifically explains a system of the planar lipid bilayer method. As illustrated in FIG. 13, an ion channel 112 is provided in an artificial lipid bilayer membrane 111, and a current flowing via the ion channel 112 is measured. The artificial lipid bilayer membrane 111 is formed on a small hole 115 provided in a partition plate 114 such as a plastic plate for parting an aqueous solution chamber 113. In one of two chambers obtained by parting the aqueous solution chamber 113, an electrode 116 is provided. Via the electrode 116, a current measuring device 117 is provided. In the other chamber, an electrode 118 is provided. Via the electrode 118, an earth 119 causes the aqueous solution chamber 113 to be earthed.

Here, examples of how to form the artificial lipid bilayer membrane 111 on the small hole 115 include (A) vertical painting method, (B) vertical applying method, (C) horizontal formation method, and the like.

In the (A) vertical painting method, first, as illustrated in the left illustration of FIG. 14, with a thin glass tube or the like, lipid solution 110 is applied to the small hole 115 provided in a support such as the plate 114 for parting the aqueous solution chamber 113 (not shown in FIG. 14). Under this condition, the lipid solution 110 swells in directions of both surfaces of the partition plate 114 so as to cover the small hole 115. The lipid solution 110 is obtained by dissolving lipid in organic solvent such as decane. After applying the lipid solution 110, the lipid solution 110 moves on the surface of the plate 114 as illustrated in the right illustration of FIG. 14, thereby obtaining an artificial lipid bilayer membrane which has become thinner in a natural manner. Note that, the wording "become thinner" means a process in which the organic solvent or the like moves from a central portion of the applied lipid solution 110 so that a lipid bilayer membrane is formed in the central portion.

Next, in the (B) vertical applying method, as illustrated in the upper illustration of FIG. 15, a lipid monomolecular membrane 121 are developed on a gas-liquid interface of the aqueous solution chamber 113 (not shown in FIG. 15). At this time, a position of the gas-liquid interface is the same as a position of a lower side end of the small hole 115 provided in the partition plate 114. Thereafter, as illustrated in the middle illustration of FIG. 15, a liquid surface (gas-liquid interface) of one chamber (right side of the middle illustration) of two chambers obtained by parting the aqueous solution chamber 113 is raised, thereby developing the monomolecular membrane 121 on the surface of the partition plate 114. On this account, one opening side of the small hole 115 is covered by the monomolecular membrane 121. Thereafter, as illustrated in the lower illustration of FIG. 15, a liquid surface (gas-liquid interface) of the other chamber (left side of the lower illustration) of two chambers obtained by parting the aqueous solution chamber 113 is raised, thereby developing the monomolecular membranes 121 on the surface of the partition plate 114. On this account, also the other opening side of the small hole 115 is covered by the monomolecular membrane 121. As a result, on each opening side of the small hole 115, the monomolecular membrane 121 is applied, so that the artificial lipid bilayer membrane 111 is finally formed.

Next, in the (C) horizontal formation method, the aqueous solution chamber 113 illustrated in FIG. 13 is vertically parted with the partition plate 114. At this time, as illustrated in FIG. 16(a), the small hole 115 provided in the partition plate 114 is covered by the lipid solution 110, and the lipid solution 110 is left until the lipid solution 110 becomes thinner in a natural manner as the artificial lipid bilayer membrane 111. Alternatively, as illustrated in FIG. 16(b), a hydraulic pressure above the small hole 115 is raised in the chamber so that the lipid solution 110 extends downward so as to be thinner, thereby forming the artificial lipid bilayer membrane 111.

However, in any one of the artificial lipid bilayer membrane formation methods, it is difficult to quickly form a stable artificial lipid bilayer membrane 111. That is, in the (A) vertical painting method, it takes several minutes to dozens minutes for the lipid solution 110 to move on the surface of the partition plate 114 and become sufficiently thinner as the artificial lipid bilayer membrane 111. Further, in the (B) vertical applying method, it is essential to carry out a pre-treatment with respect to the small hole 115 with organic solvent such as squalene before forming the artificial lipid bilayer membrane 111, so that such a larger number of steps results in a more complicate formation method. Further, it is general that the artificial lipid bilayer membrane 111 is not formed unless the liquid surface is raised and lowered several times.

Further, in the (C) horizontal formation method, in case of leaving the lipid solution 110 covering the small hole 115 until the lipid solution 110 becomes thinner in a natural manner (in case of FIG. 16(a)), it is impossible to intentionally control the formation of the artificial lipid bilayer membrane. Therefore, it sometimes takes several hours for the lipid solution 110 to become thinner. Further, in case of raising the hydraulic pressure above the small hole 115 in the chamber so that the lipid solution 110 becomes thinner (in case of FIG. 16(b)), the obtained artificial lipid bilayer membrane 111 has a thin portion serving as the "lipid bilayer membrane" and a thick portion referred to as a bulk layer surrounding the thin portion. In this manner, the artificial lipid bilayer membrane 111 obtained in this method is based on physicochemical balance of the foregoing portions. Thus, if these portions are physicochemically unbalanced by vibration caused by aqueous solution flow or the like, the artificial lipid bilayer membrane 111 is easily broken. Moreover, it is difficult to exactly control a pressure difference between the upper and lower chambers of the aqueous solution chamber 113, so that the obtained artificial lipid bilayer membrane 111 is likely to be unstable.

In case of adopting the planar lipid bilayer method, it is necessary to realize a great object: to form a stable and durable artificial lipid bilayer membrane.

The inventors of the present invention proposed a technique for solving the conventional problems in the artificial lipid bilayer membrane used in a current measuring device (for example, Non-Patent Document 2). In the current measuring device obtained by this technique, it is possible to simultaneously measure both a structure and a function of ion channel molecules by using the artificial lipid bilayer membrane.

Specifically, as illustrated in FIG. 17, the current measuring device includes two solution chambers: an upper solution chamber 101 and a lower solution chamber 102. On a central portion of a bottom of the upper solution chamber 101, a film 103 having a small hole 105 is applied. Further, the lower solution chamber 102 has an opening 104 in its bottom, and a cover glass 106 is fixed on the opening 104 with an adhesive. On the cover glass 106, an agarose gel layer (not shown) is formed.

In the current measuring device, first, a lower portion of the upper solution chamber 101 is moved in the lipid solution so as to form a thick membrane made of lipid solution in the small hole 105. Thereafter, the upper solution chamber 101 is placed in the lower solution chamber 102, and the upper solution chamber 101 is lowered so that the thick membrane formed in the small hole 105 comes into contact with the agarose gel layer formed on the cover glass 106. Here, the pressure (hydraulic pressure) in the upper solution chamber 101 is raised so that surplus lipid solution is extruded from a gap of the agarose gel layer, so that an artificial lipid bilayer membrane is formed by making the thick membrane thinner.

In the current measuring device, the pressure in the upper solution chamber 101 is raised, so that it takes less time to form an artificial lipid bilayer membrane (to make the thin membrane thinner). The thus formed artificial lipid bilayer membrane is supported by the agarose gel layer. Thus, even when a pressure is exerted by the upper solution chamber 101, the artificial lipid bilayer membrane is stabilized in upward and downward directions.

[Non-Patent Document 1]
"New Patch-Clamp Test" written by Shigetoshi Oiki, published by Yoshioka-shoten, 2001, pages 208-215, "19. planar lipid bilayer method for Studying Channel"

[Non-Patent Document 2]
Ide, T., Takeuchi, U., Yanagida, T. Development of an Experimental Apparatus for Simultaneous Observation of Optical and Electrical Signals from Single Ion Channels, Single Mol. 3(2002) 1, pages 33-42

However, in the conventional technique for forming the artificial lipid bilayer membrane, it is sometimes difficult to stably form the artificial lipid bilayer membrane, so that a more stable formation technique is required.

Specifically, in the conventional technique, the pressure (hydraulic pressure) in the upper solution chamber 101 is raised so that surplus lipid solution is extruded from a gap of the agarose gel layer, thereby making the thick membrane thinner. At this time, when the pressure of the upper solution chamber 101 is raised, as illustrated in FIG. 18(a), the surplus lipid moves away in R directions between the bottom of the upper solution chamber 101 and the agarose gel layer 108, so that it is possible to make the thick membrane thinner. However, as illustrated in FIG. 18(b), a higher pressure in the upper solution chamber 101 allows the aqueous solution to move from the upper solution chamber 101 to the lower solution chamber 102 (in M directions). Thus, as illustrated in FIG. 18(c), the artificial lipid bilayer membrane 111 having been made thinner is likely to excessively expand and is likely to be broken.

In case where the thick membrane made of lipid solution so as to cover the small hole is made thinner in this manner, when a technique of raising the pressure in the upper solution chamber is adopted, there occurs such problem that it is impossible to make the thick membrane thinner in a stable manner and the artificial lipid bilayer membrane is likely to be broken.

DISCLOSURE OF INVENTION

The present invention was made in view of the foregoing problems, and an object of the present invention is to provide (i) an artificial lipid bilayer membrane formation device, (ii) an artificial lipid bilayer membrane formation method, whereby it is possible to quickly form a stable artificial lipid bilayer membrane and it is possible to simultaneously measure a structure and a function of a single ion channel for example, and (iii) an example of a typical usage thereof.

An artificial lipid bilayer membrane formation device according to the present invention includes: a membrane support whose plate portion has a membrane formation opening; and a membrane formation solution chamber which is capable of containing aqueous solution, the membrane formation solution chamber having a support layer for supporting an artificial lipid membrane, the artificial lipid bilayer membrane being formed on the membrane formation opening of the membrane support and being brought into contact with the support layer so as to be supported, and the artificial lipid bilayer membrane formation device is characterized by further including lipid solution exclusion means for excluding surplus lipid solution from lipid solution applied to the membrane formation opening without changing a hydraulic pressure, wherein: the membrane support is placed in the membrane formation solution chamber so that at least one side of the membrane formation opening is in contact with the aqueous solution, and the lipid solution is applied to the membrane formation opening, and the lipid solution is sandwiched by the aqueous solution and the support layer so as to be in contact with the support layer, and the lipid solution exclusion means excludes the surplus lipid solution under this condition so as to form the artificial lipid bilayer membrane on the membrane formation opening.

According to the foregoing arrangement, the lipid solution exclusion means is provided, so that it is possible to exclude the surplus lipid solution from the lipid solution applied to the membrane formation opening without changing the hydraulic pressure. Thus, no pressure is exerted onto the membrane, so that the membrane is free from any breakage or any unstable condition in making the membrane thinner. Thus, it is possible to quickly form a stable and highly durable artificial lipid bilayer membrane.

An artificial lipid bilayer membrane formation method according to the present invention includes the steps of: (i) applying lipid solution to a membrane formation opening provided in a plate portion of a membrane support so that at least one side of the membrane formation opening is in contact with aqueous solution; (ii) bringing the lipid solution applied to the membrane formation opening into contact with a support layer whose surface is hydrophilic by sandwiching the lipid solution between the aqueous solution and the support layer; and (iii) making an artificial lipid bilayer membrane thinner, formed on the membrane formation opening, by excluding surplus lipid solution from the lipid solution applied to the membrane formation opening without changing a hydraulic pressure.

According to the foregoing arrangement, it is possible to exclude the surplus lipid solution from the lipid solution applied to the membrane formation opening without changing the hydraulic pressure. Thus, no pressure is exerted onto the membrane, so that the membrane is free from any breakage or any unstable condition in making the membrane thinner. Thus, it is possible to quickly form a stable and highly durable artificial lipid bilayer membrane.

A current measuring device according to the present invention is produced by using the artificial lipid bilayer membrane formation device according to the present invention.

According to the foregoing arrangement, it is possible to use a stable artificial lipid bilayer membrane in measuring a current via the membrane, so that it is possible to measure a current with high accuracy.

For a fuller understanding of the nature and advantages of the invention, reference should be made to the ensuing detailed description taken in conjunction with the accompanying drawings.

BEST MODE FOR CARRYING OUT THE INVENTION

Embodiment 1

The following explains one embodiment of the present invention with reference to FIGS. 1 through 4. Note that, the present invention is not limited by the following embodiment.

(1) An Example of an Artificial Lipid Bilayer Membrane

Figure 1:
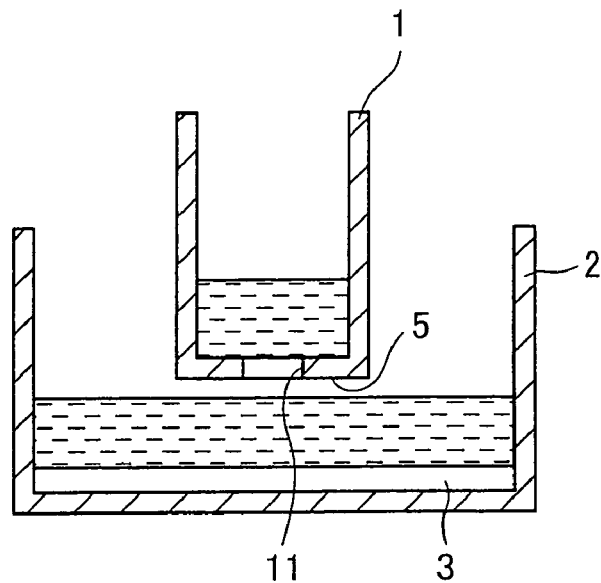
FIG. 1 is a cross sectional view illustrating a structure of an artificial lipid bilayer membrane formation device of one embodiment according to the present invention.

As illustrated in FIG. 1, an artificial lipid bilayer membrane formation device according to the present invention (hereinafter, referred to also as a formation device as required) includes at least an upper solution chamber 1, a lower solution chamber (membrane formation solution chamber) 2, a support layer 3, and a sucking section (sucking means: not shown). The sucking section functions as lipid solution exclusion means for excluding surplus lipid solution from lipid solution applied to a membrane formation opening without changing a hydraulic pressure. Further, a bottom of the upper solution chamber 1 serves as a membrane support 5, and an artificial lipid bilayer membrane is formed on a small hole (membrane formation opening) 11 provided in the membrane support 5.

<Membrane Support>

A specific structure of the membrane support 5 is not particularly limited as long as the small hole 11 serving as the membrane formation opening is provided in a plate portion. In the present embodiment, as illustrated in FIG. 1, the membrane support 5 is a bottom of the upper solution chamber 1 which can contain the solution.

The membrane support 5 is not particularly limited as long as the membrane support 5 has a plate shape or a film shape. Thus, in case where the membrane support 5 is the bottom of the upper solution chamber 1, it may be so arranged that the small hole 11 is provided in the bottom of the upper solution chamber 1, or it may be so arranged that an opening is provided in the bottom of the upper solution chamber 1 and a film having the small hole 11 is combined to the opening.

A material of the membrane support 5 is not particularly limited, but specific favorable examples thereof include plastic, fluorine, and the like, e.g., polypropylene, polyvinylchloride, and polystyrene. Further, it is preferable that the thickness of the membrane support 5 is 0.1 mm or more and 0.3 mm or less. Note that, only a portion around the small hole 11 is made thinner than other portion, thereby quickly forming a stable artificial lipid bilayer membrane. A diameter of the small hole 11 is preferably 10 µm or more and 500 µm or less, more preferably 50 µm or more and 200 µm or less. On this account, it is possible to favorably form the artificial lipid bilayer membrane.

The small hole 11 can be formed by the following conventional known method for example. First, a stainless rod which has been pointed into a sharp cone is heated with a gas burner or the like. Subsequently, the heated stainless rod is firmly pressed against a surface in which the small hole 11 is to be formed. The pressing of the stainless rod is continued until a back surface of the pressed surface slightly swells. This slightly swelling portion is cut with a razor, thereby providing the small hole 11. Note that, the small hole 11 is rinsed with chloroform/methanol so that impurities and the like are removed. Of course, a method for providing the small hole 11 is not limited to this, and any known method can be applied.

<Upper Solution Chamber>

The upper solution chamber 1 is provided above the lower solution chamber 2 and can contain aqueous solution. An arrangement of the upper solution chamber 1 is not particularly limited as long as the membrane support 5 is the bottom of the upper solution chamber 1.

A shape of the upper solution chamber 1 is not particularly limited, but an example thereof is a cylindrical shape. Further, a size of the upper solution chamber 1 is particularly limited as long as the upper solution chamber 1 is larger than the small hole 11. However, in case where the upper solution chamber 1 has a cylindrical shape for example, its internal diameter is preferably 0.5 mm or more and 20 mm or less, more preferably 1.0 mm or more and 10 mm or less. Further, the size of the upper solution chamber 1 can be reduced so that the internal diameter is preferably dozens µm or more. Further, a volume of the upper solution chamber 1 is not particularly limited, but it is preferable that the volume is 0.01 $cm^3$ or more and 1.0 $cm^3$ or less. On this account, it is possible to provide the artificial lipid bilayer membrane formation device according to the present invention on a small-size chip, so that it is possible to manufacture a smaller sensor.

Further, in the upper solution chamber 1, a material of a portion other than the portion in which the small hole 11 is provided (that is, a portion other than the membrane support 5) is not particularly limited, but examples thereof include glass, plastic, and the like.

The upper solution chamber 1 can contain the aqueous solution. Each side of the artificial lipid bilayer membrane formed on the small hole 11 is in contact with the aqueous solution with which the upper solution chamber 1 and the lower solution chamber 2 are filled. This condition is not different in a case where the artificial lipid bilayer membrane's portion positioned on the side of the lower solution chamber 2 is in contact with the support layer 3. That is, the artificial lipid bilayer membrane is in contact with the aqueous solution penetrating the support layer 3. This allows small molecules to access from beneath of the artificial lipid bilayer membrane. The aqueous solution is not particularly limited as long as the aqueous solution does not include surfactant, organic solvent, and the like. A favorable example of the aqueous solution is aqueous solution of potassium chloride, sodium chloride, calcium chloride, or the like.

Further, it is preferable that the upper solution chamber 1 can be moved in upward and downward directions. The upper solution chamber 1 may be moved in upward and downward directions manually or by using a moving instrument. A specific example of the moving instrument is a micro manipulator or the like.

<Lower Solution Chamber>

The lower solution chamber 2 may be arranged in any manner as long as: the lower solution chamber 2 is disposed under the upper solution chamber 1, and can contain the aqueous solution, and serves as a membrane formation solution chamber for forming the membrane support 5. On a bottom of the lower solution chamber 2, the support layer 3 for supporting the artificial lipid bilayer membrane is provided. Further, the artificial lipid bilayer membrane formed on the small hole 11 in the upper solution chamber 1 is brought into contact with the support layer 3 so as to be supported.

A volume of the lower solution chamber 2 is not particularly limited as long as the upper solution chamber 1 can be placed on the formed support layer 3.

A material of the lower solution chamber 2 is not particularly limited, but examples thereof include glass and plastic such as polystyrene and the like.

Further, as in the aqueous solution in the upper solution chamber 1, the aqueous solution does not include a surfactant, organic solvent, and the like. A favorable example of the aqueous solution is aqueous solution of potassium chloride, sodium chloride, calcium chloride, or the like.

<Support Layer>

The support layer 3 provided on the bottom of the lower solution chamber 2 may be arranged in any manner as long as the artificial lipid bilayer membrane formed on the small hole 11 in the membrane support 5 is brought into contact with the support layer 3 so as to be supported.

The support layer 3 is not particularly limited as long as the aqueous solution can permeate the support layer 3 and the support layer 3 can support the artificial lipid bilayer membrane 2. A specific example of the support layer 3 is a porous membrane such as a polymer gel membrane, a cellulose membrane, and the like. Among them, it is more preferable that the support layer 3 is made of polymer gel. The polymer gel is not particularly limited, but a polysaccharide such as agarose and a hydrophilic resin such as polyacrylamide can be favorably used. By using these materials, it is possible to easily form the support layer 3 with inexpensive and highly reliable materials.

The support layer 3 may have any thickness, but the thickness is preferably 100 nm or more and 2 mm or less. The thickness of the support layer 3 is in this range, so that the formed artificial lipid bilayer membrane is stabilized in upward and downward directions.

Further, a method for forming the support layer 3 is not particularly limited, and a conventional known method may be used. A specific example thereof is as follows: in case of using agarose (polymer gel) as the support layer 3, agarose dispersion liquid is prepared, and the thus prepared liquid is heated so that agarose is dissolved, and then the liquid is applied to the bottom of the lower solution chamber 2, and the applied liquid is dried at a room temperature.

<Artificial Lipid Bilayer Membrane>

The artificial lipid bilayer membrane is formed on the small hole 11 provided in the bottom 5 of the upper solution chamber 1. As will be described alter, the artificial lipid bilayer membrane is formed as follows: the lipid solution is applied to the small hole 11, and the applied lipid solution is brought into contact with the support layer 3 of the lower solution chamber 2, and surplus lipid solution is sucked by the sucking section.

The lipid is not particularly limited as long as the lipid constitutes the artificial lipid bilayer membrane, but phospholipid is favorably used. Specific examples thereof include phosphatidylcholine, diphytanoil phosphatidylcholine, phosphatidylethanolamine, phosphatidylcerine, and the like.

Two hydrocarbon chains of the phospholipid may be saturated hydrocarbon or may be unsaturated hydrocarbon. As the lipid, pure lipid may be used or a mixture of two or more kinds of the lipids may be used.

The lipid solution is a solution obtained by dispersing the lipid in organic solvent. The organic solvent used is not particularly limited as long as the organic solvent is nonpolar organic solvent. As a specific example thereof, unsaturated hydrocarbon such as decane, hexadecane, and hexane is favorably used. Further, the lipid concentration preferably ranges from 5 to 40 mg/mL, more preferably from 15 to 20 mg/mL.

<Sucking Section>

The sucking section may be arranged in any manner as long as it is possible to exclude surplus lipid solution from the lipid solution applied to the small hole 11 by sucking the surplus lipid solution.

Figure 2:
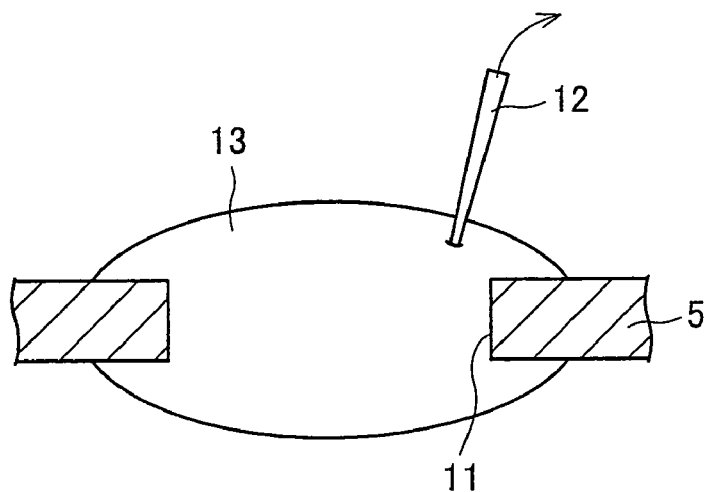
In FIG. 2, (a) is a partially cross sectional view illustrating a state in which lipid solution is applied to a small hole of an upper solution chamber and surplus lipid solution is sucked by a sucking section in the artificial lipid bilayer membrane formation device of FIG. 1. (b) is a partially cross sectional view illustrating a state in which the surplus lipid solution is sucked so as to form an artificial lipid bilayer membrane.
Figure 2:
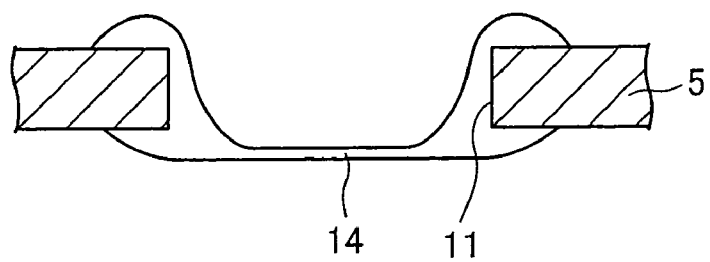

How the membrane is made thinner by the sucking section is described as follows with reference to FIG. 2.

The lipid solution is applied to the small hole 11 of the membrane support 5. As will be described later, the lipid solution 13 is sandwiched by the aqueous solution and the support layer so as to be brought into contact with the support layer. Under this condition, surplus lipid solution 13 is excluded by using the sucking section 12 so that an artificial lipid bilayer membrane 14 having made thinner is formed on the small hole 11.

The sucking section 12 may be made of any material as long as the material has a tubular shape which can suck the surplus lipid solution 13, other than the lipid solution required in forming the lipid bilayer membrane, from the lipid solution 13 applied to the portion around the small hole 11. Examples thereof include a glass tube connected to an injection syringe, a silicon dropper, and the like.

Figure 3:
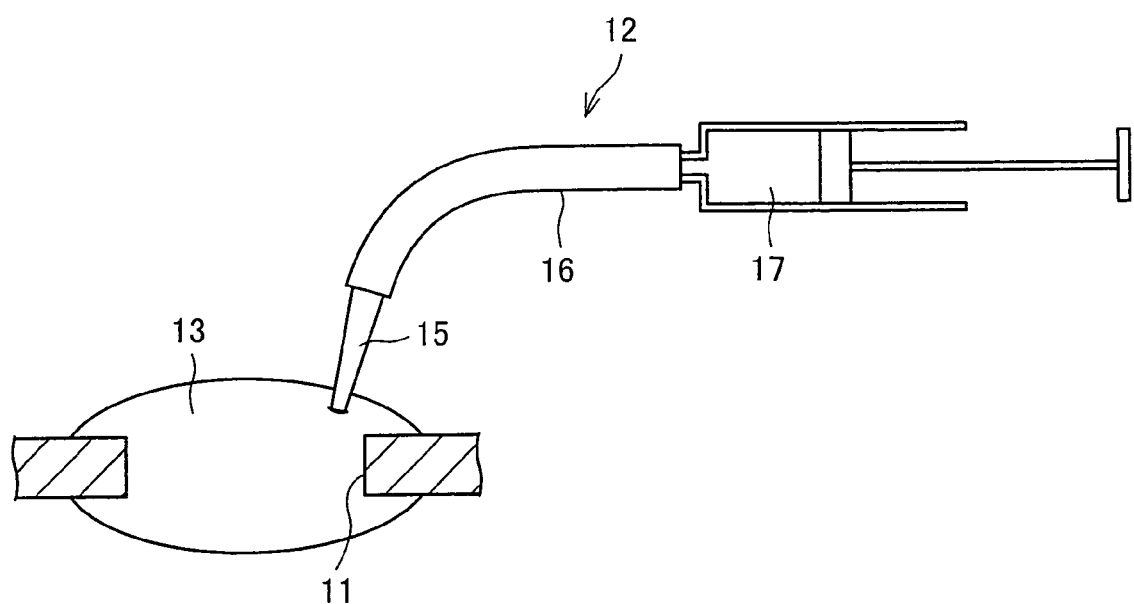
FIG. 3 is a cross sectional view illustrating an example of a structure of the sucking section in the artificial lipid bilayer membrane formation device of FIG. 1.

For example, as illustrated in FIG. 3, a glass tube 15 having been thermally extended so as to trail is connected to the lipid solution 13, and an injection syringe 17 connected to a silicon tube 16 is used, thereby sucking the surplus lipid solution 13. In sucking the lipid solution 13, it is preferable to suck the lipid solution 13 on a portion around the opening first, and it is particularly preferable to suck the lipid solution 13 on the bulk portion first, so as to form the lipid bilayer membrane without breaking the membrane.

(2) An Example of an Artificial Lipid Bilayer Membrane Formation Method

Figure 4:
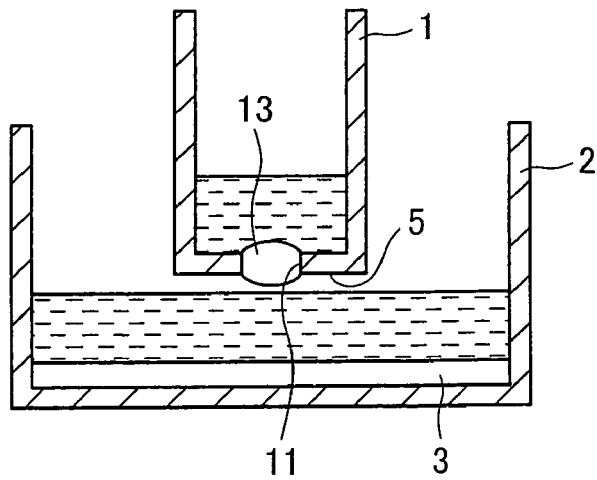
In FIG. 4, (a) to (c) are cross sectional views each of which illustrates a step in an artificial lipid bilayer membrane formation method of one embodiment according to the present invention.
Figure 4:
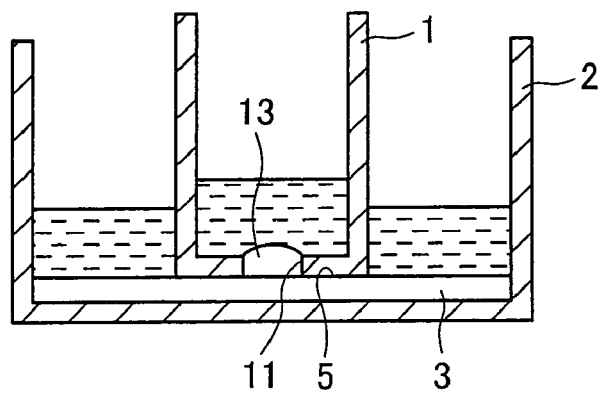
Figure 4:
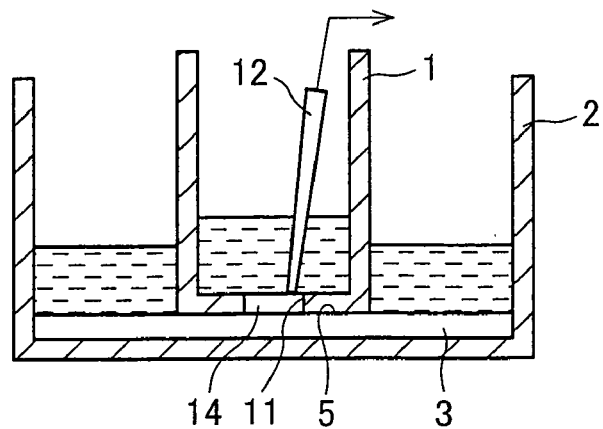

As the artificial lipid bilayer membrane formation method according to the present invention, with reference to FIG. 4(*a*) to (*c*), the following explains a case where the artificial lipid bilayer membrane formation device explained in the foregoing example (1) is used.

First, the step of applying the lipid solution (step (i)) is explained. As illustrated in FIG. 4(*a*), the support layer 3 is formed on the bottom of the lower solution chamber 2, and the upper solution chamber 1 and the lower solution chamber 2 are filled with the aqueous solution. Further, the lipid solution 13 is applied to the small hole 11 provided in the membrane support which is the bottom of the upper solution chamber 1.

Next, the step of bringing the lipid solution into contact with the support layer (step (ii)) is explained. As illustrated in FIG. 4(*b*), the bottom of the upper solution chamber 1 is placed in the lower solution chamber 2 so as to be in contact with the support layer 3, and the lipid solution 13 applied to the small hole 11 in the step (i) is sandwiched by the aqueous solution in the upper solution chamber 1 and the support layer 3. On this account, the applied lipid solution 13 can be brought into contact with the support layer 3.

Next, the step of making the lipid membrane thinner (step (iii)) is explained. As illustrated in FIG. 4(*c*), the sucking section 12 having a tubular member is attached to the lipid solution 13 brought into contact with the support layer 3, and surplus lipid solution 13 is sucked so as to be excluded as described above, thereby forming the thinner artificial lipid bilayer membrane 14 on the small hole 11.

In this manner, the surplus lipid solution 13 is excluded from the lipid solution 13 applied to the small hole 11 without changing the hydraulic pressure, that is, without raising the hydraulic pressure exerted to the lipid solution 13 unlike the conventional technique, so that it is possible to form the artificial lipid bilayer membrane on the small hole 11 so that the artificial lipid bilayer membrane is in contact with the support layer 3. Further, the bottom of the upper solution chamber 1 has the opening, and the bottom of the lower solution chamber 2 is closed. Thus, the artificial lipid bilayer membrane is stabilized in a direction parallel to the bottom unlike the conventional technique, so that it is possible to further improve the durability of the artificial lipid bilayer membrane.

(3) Use of the Present Invention

As described above, the artificial lipid bilayer membrane formation device according to the present invention can form a stable and highly durable artificial lipid bilayer membrane in short time. Further, also an artificial lipid bilayer membrane formed by using the artificial lipid bilayer membrane formation device according to the present invention is included in the present invention.

By utilizing any change of the artificial lipid bilayer membrane (for example, changes of a membrane potential, electric capacitance, ion permeability, light emission, heat generation, an endothermal property, and the like), it is possible to detect whether there is any dissolved substance in the sample liquid or not and its concentration. Examples of the lipid bilayer membrane include: an artificial lipid bilayer membrane made substantially only of lipid; an artificial lipid bilayer membrane obtained by causing molecules such as various kinds of proteins and sugars to adhere or by blending molecules such as various kinds of proteins and sugars; and the like. By suitably selecting a kind and an amount of lipid, proteins, and sugars, and by selecting a formation method of the lipid bilayer membrane, it is possible to produce various kinds of sensors according to an object of measurement or according to specific contents such as a sample liquid.

As described above, as the artificial lipid bilayer membrane obtained by causing molecules such as various kinds of proteins and sugars to adhere or by blending molecules such as various kinds of proteins and sugars, an artificial lipid bilayer membrane including membrane proteins may be used.

An example of the membrane proteins is an ion channel. A method for providing the ion channel in the artificial lipid bilayer membrane is not particularly limited, and a conventional known method can be applied. A specific example thereof is a method in which: a membrane fraction including an ion channel is made soluble with surfactant, and the membrane fraction is rearranged into a membrane vesicle, and the membrane vesicle is fused with the artificial lipid bilayer membrane.

Figure 5:
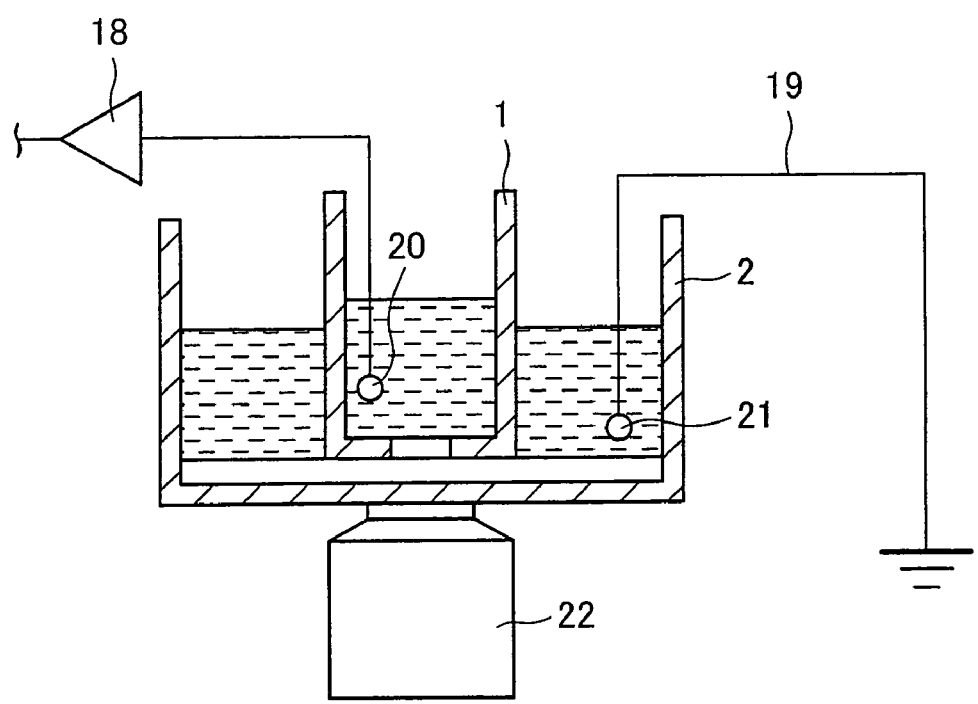
FIG. 5 is a cross sectional view illustrating a current measuring device of one embodiment according to the present invention.

It is possible to produce a current measuring device by using the artificial lipid bilayer membrane formation device, and also the current measuring device is included in the present invention. An arrangement of the current measuring device is not particularly limited as long as the current measuring device can measure a current flowing via the artificial lipid bilayer membrane. For example, as illustrated in FIG. 5, the current measuring device of the present embodiment includes not only a mechanism of the artificial lipid bilayer membrane illustrated in FIG. 1 but also a current measuring instrument (current measuring means) 18 electrically connected to the upper solution chamber 1 and an earth (earthing means) 19 electrically connected to the lower solution chamber 2. Note that, the current measuring device is not limited to the foregoing arrangement. In the upper solution chamber 1, an electrode 20 is placed, and the current measuring instrument 18 is provided via the electrode 20. In the lower solution chamber, an electrode 21 is placed. Via the electrode 21, the lower solution chamber 2 is earthed with the earth 19.

Further, it may be so arranged that: the bottom of the lower solution chamber 2 is made of translucent material, and optical observation means 18 which allows observation of the artificial lipid bilayer membrane on the support layer 3 is provided below the bottom. In case where membrane proteins are included in the artificial lipid bilayer membrane for example, the optical observation means 20 allows observation of a structure and the like of the membrane proteins.

An example of the optical observation means is an optical microscope. Examples of observation through the optical microscope include: observation of change in fluorescent intensity of a fluorescence-labeled ion channel upon opening/closing a gate; observation of movement of the ion channel; observation of spectrum change caused by energy transfer between two fluorescent dyes; and the like. Further, it is possible to confirm the formation of the artificial lipid bilayer membrane through the optical microscope. In addition, it is possible to observe movement of lipid molecules by using the artificial lipid bilayer membrane having a fluorescence-labeled lipid. Of course, the optical measurement is not limited to them, and any conventional known method can be applied.

The artificial lipid bilayer membrane formation device of the present invention can further stabilize the formed artificial lipid bilayer membrane, so that it is possible to simultaneously measure a structure and a function of the membrane proteins in a sufficiently stable manner even under such condition that the membrane proteins are included in the artificial lipid bilayer membrane.

An example of specific use of the current measuring device according to the present invention is described as follows: it is possible to use the current measuring device in screening a drug made by using ion channel proteins concerning a certain disease.

There are many kinds of ion channel proteins, and the ion channel proteins distribute in substantially all the cells. Thus, these ion channel proteins are likely to cause the disease, and it is said that 30 to 40% of targets in making a drug are ion channel proteins. Generally, a pharmacological test is carried out to confirm an effect obtained by administering a reagent to an experimental animal. If it is possible to form a stable artificial lipid bilayer membrane 2, it is possible to carry out screening in making a drug while directly examining an effect exerted to a target ion channel. Particularly, most of drugs such as psychoactive drugs for acting upon a nerve system directly act upon the ion channel proteins, so that the current measuring device can be favorably adopted to the drug making in this field. Adversely, the current measuring device can be used to select a substance which does not act upon the human ion channel in making an agrichemical.

Further, the current measuring device according to the present invention can be used to carry out visual analysis of protein-protein (drug) interaction on the artificial lipid bilayer membrane. Moreover, by changing a type of molecules included in the artificial lipid membrane, it is possible to apply the current measuring device to detection of various substances.

Embodiment 2

Another embodiment of the present invention is described as follows. Note that, the present invention is not limited only to the present embodiment. Further, explanations of members and the like having the same functions and effects as those of members explained in Embodiment 1 are omitted.

(1) Another Example of the Artificial Lipid Bilayer Membrane Formation Device

An artificial lipid bilayer membrane formation device according to the present embodiment is arranged in the same manner as the artificial lipid bilayer membrane formation device illustrated in FIG. 1 (Embodiment 1) except that: there is no sucking section, and a movable membrane support excludes surplus lipid solution from the lipid solution applied to the opening without changing the hydraulic pressure. In the present embodiment, the movable membrane support functions as the lipid solution exclusion means. Further, the support layer functions in a different manner as will be described later.

<Movable Membrane Support>

The movable membrane support is not particularly limited as long as the movable membrane support can move in a direction in which the support layer provided on the lower solution chamber 2 is pressed. In the present embodiment, as in Embodiment 1, the movable membrane support is a bottom portion of the upper solution chamber 1 which can contain the solution.

Figure 6:
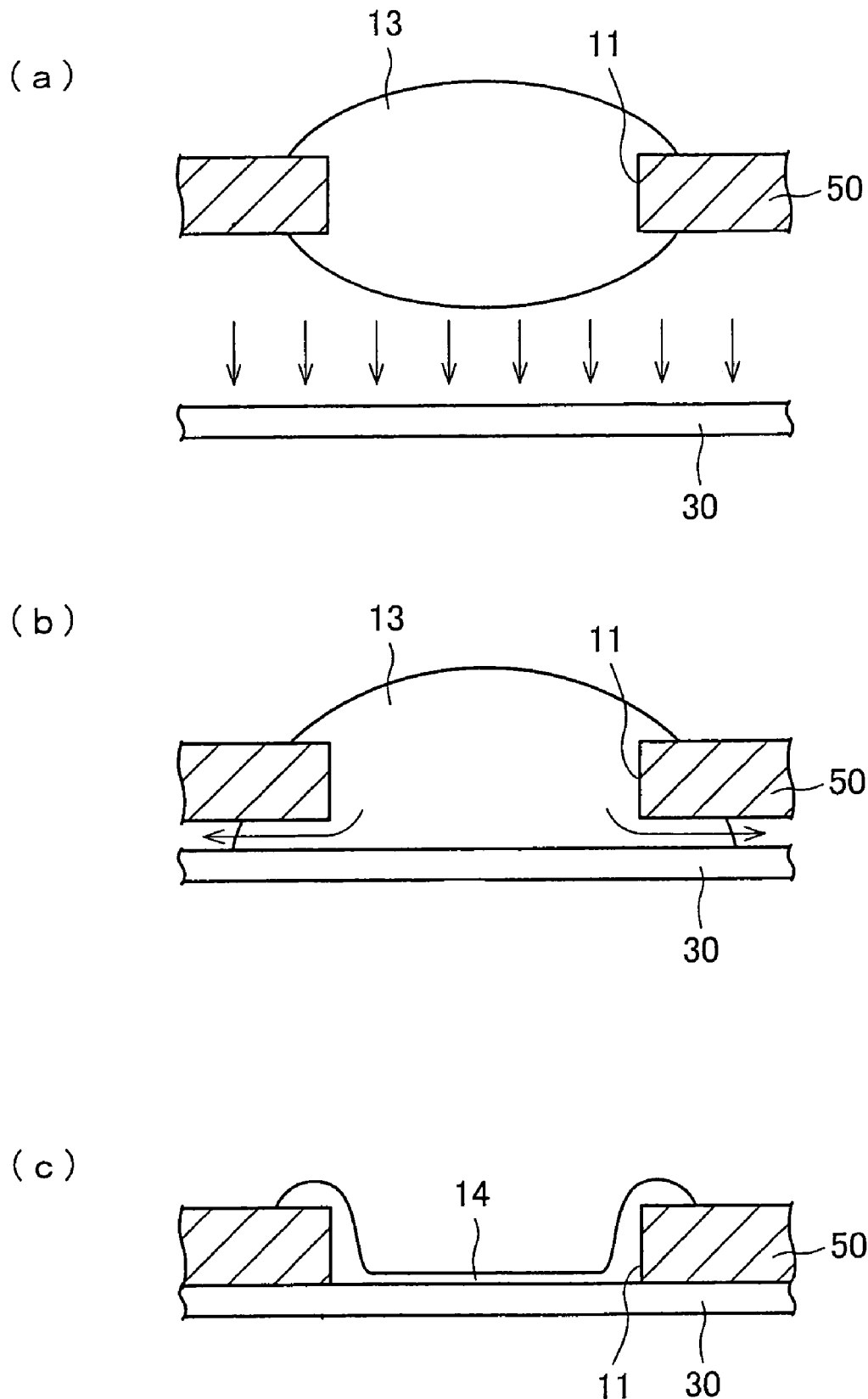
In FIG. 6, (a) to (c) are partially cross sectional views each of which illustrates a small hole and a support layer of an artificial lipid bilayer membrane formation device of another embodiment according to the present invention. (a) illustrates a state in which lipid solution is applied to a small hole of an upper solution chamber. (b) illustrates a state in which the lipid solution is kept in contact with a support layer. (c) illustrates a state in which an artificial lipid bilayer membrane is formed.

As illustrated in FIG. 6, a movable membrane support 50 is used as the lipid solution exclusion means, and the lipid solution 13 applied to the small hole 11 of the membrane support 50 is pressed against the support layer 30 so as to extrude the lipid solution 13, thereby excluding the surplus lipid solution from the lipid solution 13 applied to the small hole 11 without changing the hydraulic pressure. The lipid solution 13 is pressed against the support layer 30, so that the lipid solution 13 passes through a gap between the movable membrane support 50 and the support layer 30 and is extruded, thereby making the artificial lipid bilayer membrane thinner.

It is preferable that the movable membrane support 50 can move in upward and downward directions. In the present embodiment, the membrane support 50 is a bottom of the upper solution chamber 1, so that the membrane support 50 moves in combination with the upper solution chamber 1. The upper solution chamber 1 may be moved in upward and downward directions manually or by using a moving instrument. A specific example of the moving instrument is a micro manipulator or the like.

<Support Layer>

As in Embodiment 1, the support layer 30 may be arranged in any manner as long as: the support layer 30 is provided on the bottom of the lower solution chamber 2, and the artificial lipid bilayer membrane formed on the small hole 11 provided in the membrane support 50 is brought into contact with the support layer 30 so as to be supported. The support layer 30 is pressed via the movable membrane support 50, so that it is preferable that the support layer 30 has elasticity.

An example of the support layer 30 is a polymer gel layer as in Embodiment 1. It is preferable that the thickness of the polymer gel layer is 0.5 mm or more and 2.0 mm or less. When the polymer gel layer has such thickness, it is possible to favorably extrude the surplus lipid solution 13 in pressing the lipid solution 13 applied to the small hole 11 provided in the membrane support 50.

Figure 7:
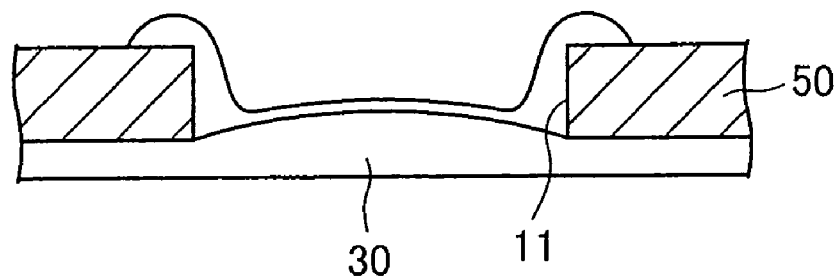
In FIG. 7, (a) is a partially cross sectional view illustrating a state in which a membrane support having the lipid solution is pressed against a polymer gel and the polymer gel enter the small hole so that an artificial lipid bilayer membrane is formed. (b) is a partially cross sectional view illustrating a state in which an artificial lipid bilayer membrane is formed on the polymer gel whose portion contacting the small hole is higher than other portion.
Figure 7:
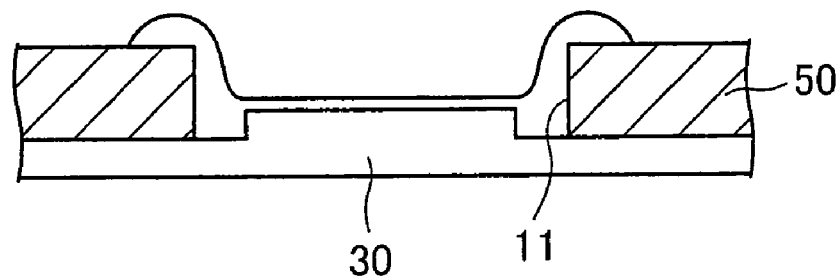

In case where the support layer 30 is the polymer gel layer when the movable membrane support 50 having the lipid solution is pressed against the support layer 30, a shape of the support layer 30 changes, so that the support layer 30 swells into the small hole 11 as illustrated in FIG. 7(a). Thus, as illustrated in FIG. 7(b), it may be so arranged that the support layer 30 has a higher portion contacting the small hole 11 than other portions by 50 μm or more and 200 μm or less. The support layer 30 has the higher portion in this manner, so that it is possible to plug the support layer 30 into the small hole 11. Thus, the support layer 30 can be favorably brought into contact with the lipid bilayer membrane, so that it is possible to form a stable artificial lipid bilayer membrane.

(2) Another Example of the Artificial Lipid Bilayer Membrane Formation Method

Figure 8:
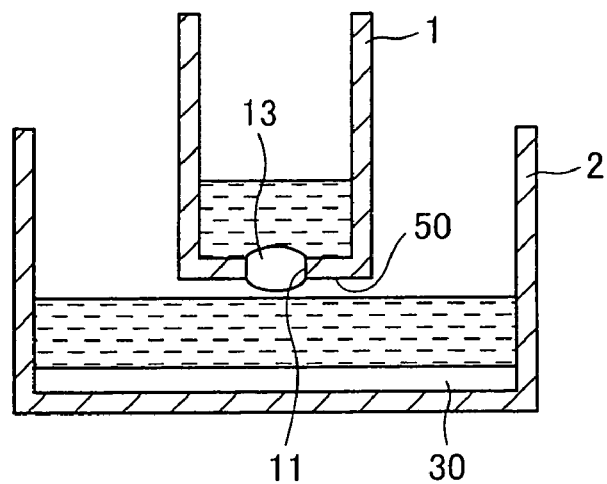
In FIG. 8, (a) to (c) are cross sectional views each of which illustrates a step in an artificial lipid bilayer membrane formation method of another embodiment according to the present invention.
Figure 8:
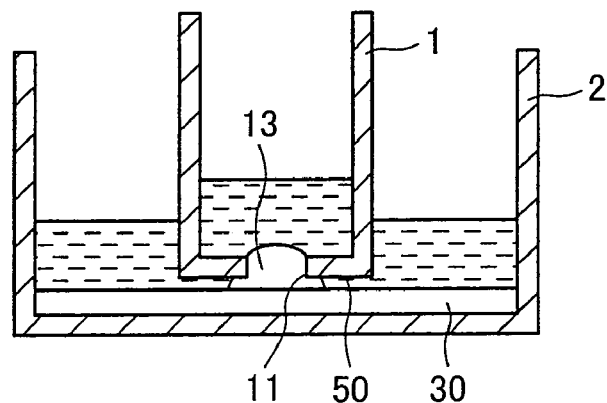
Figure 8:
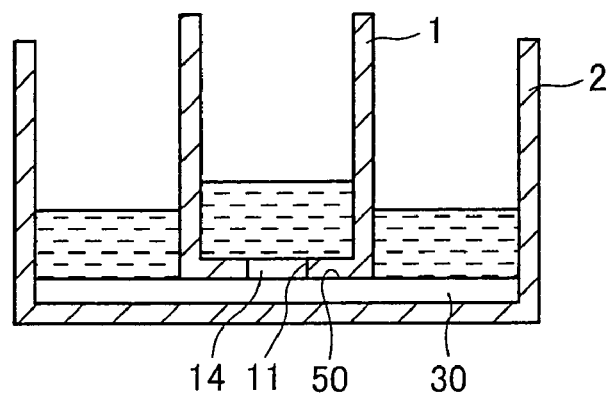

As another artificial lipid bilayer membrane formation method according to the present invention, with reference to FIG. 8(a) to (c), the following explains a case where the artificial lipid bilayer membrane formation device explained in the foregoing example (1) is used.

First, the step of applying the lipid solution (step (i)) is explained. As illustrated in FIG. 8(a), the support layer 30 is formed on the bottom of the lower solution chamber 2 in advance, and the upper solution chamber 1 and the lower solution chamber 2 are filled with the aqueous solution. Further, the lipid solution 13 is applied to the small hole 11 provided in the membrane support 50 which is the bottom of the upper solution chamber 1.

Next, the step of bringing the lipid solution 13 into contact with the support layer (step (ii)) is explained. As illustrated in FIG. 8(b), the bottom of the upper solution chamber 1 is placed in the lower solution chamber 2 so as to be brought into contact with the support layer 30, and the lipid solution 13 applied to the small hole 11 in the step (i) is sandwiched by the aqueous solution in the upper solution chamber 1 and the support layer 30. On this account, the applied lipid solution 13 can be brought into contact with the support layer 30.

Next, the step of making the lipid membrane thinner (step (iii)) is explained. As illustrated in FIG. 8(c), the movable membrane support 50 is pressed against the support layer 30, so that the lipid solution 13 is pressed against the support layer 30, thereby excluding the lipid solution 13. The lipid solution 13 is pressed against the support layer 30 so as to pass through a gap between the membrane support 50 and the support layer 30, so that the lipid solution 13 is extruded, thereby making the artificial lipid bilayer membrane thinner.

In this manner, the surplus lipid solution 13 is excluded from the lipid solution 13 applied to the small hole 11 without changing the hydraulic pressure, thereby forming the artificial lipid bilayer membrane on the small hole 11 so that the artificial lipid membrane is in contact with the support layer 30. Further, the bottom of the upper solution chamber 1 has the opening, and the bottom of the lower solution chamber 2 is closed. Thus, the artificial lipid bilayer membrane is stabilized in a direction parallel to the bottom unlike the conventional technique, so that it is possible to further improve the durability of the artificial lipid bilayer membrane.

EXAMPLES

The following description further details the present invention with reference to Examples and FIGS. 9 through 13, but the present invention is not limited to them. In the following Examples, a current measuring device including the artificial lipid bilayer membrane formation device explained in Embodiment 1 (illustrated in FIG. 5) was used. As illustrated in FIG. 5, a propylene chamber whose volume was 0.1 cm$^3$, bottom thickness was 0.2 mm to 0.3 mm, and small hole 11 had a diameter of 0.15 mm, was used as the upper solution chamber 1. On the bottom of the lower solution chamber 2, an agarose gel layer whose thickness was 150 nm was formed as the support layer 3. As the aforementioned electrode, an Ag—AgCl electrode obtained by plating an Ag foil with Ag was used. Further, a glass tube connected to a silicon tube was used as the sucking section for making the lipid thinner. In measuring a current, a patch-clamp amplifier (CEZ-2400 produced by Nihon Kohden Corporation) was used, and the measured current was recorded on a DAT tape by using a DAT recorder.

Example 1

Single Channel Current Record of Plain Muscle Ca$^{2+}$ Dependency K-Channel

First, the upper solution chamber 1 and the lower solution chamber 2 were filled with aqueous solution made of 100 mM KCl, 1 mM CaCl$_2$ (or 10$^{-9}$ M CaCl$_2$), 10 mM Hepes (pH 7.4).

Figure 9:
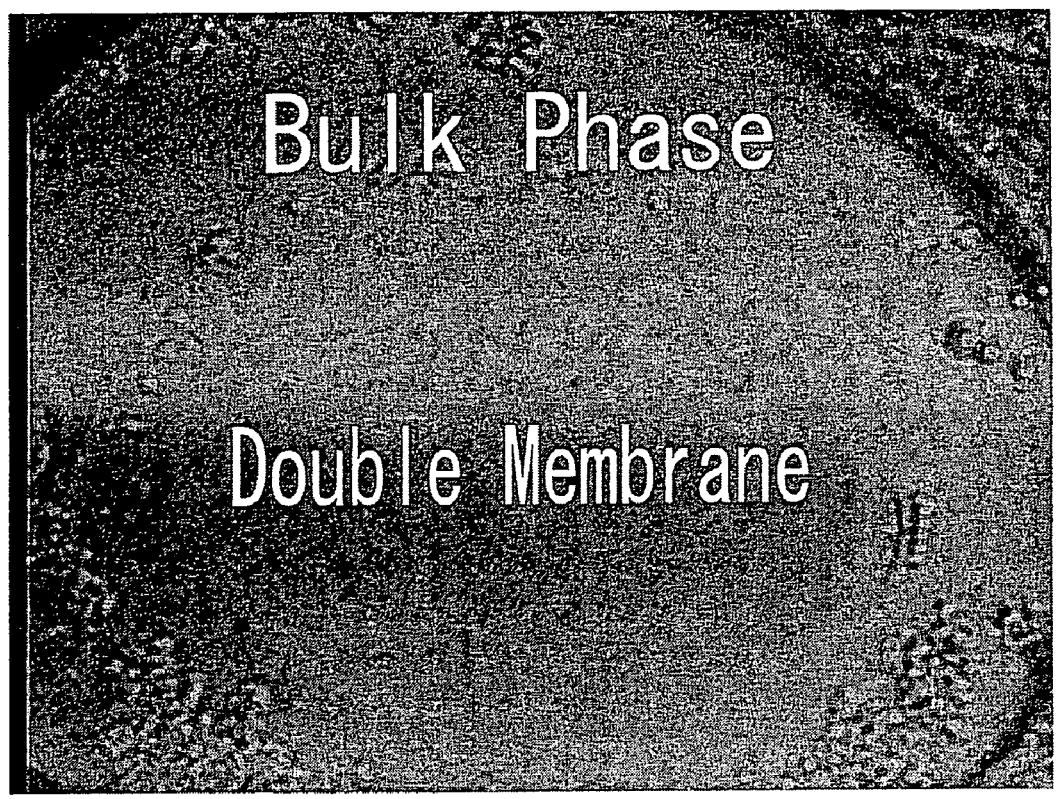
FIG. 9 is a photograph indicative of a state in which making an artificial lipid bilayer membrane thinner is completed in Example 1.

Thereafter, lipid solution obtained by dissolving phosphatidylcholine (product of Sigma) in decane so that its concentration was 20 mg/mL was applied to the small hole 11 provided in the membrane support 5 of the upper solution chamber 1. After the application, the bottom of the upper solution chamber 1 was brought into contact with the agarose gel layer (support layer 3) of the lower solution chamber 2. Further, the glass tube was brought into contact with the lipid solution applied to the small hole 11, and surplus phosphatidylcholine decane solution was sucked, thereby forming an artificial lipid bilayer membrane. Through a microscope, it was observed that the artificial lipid bilayer membrane 2 was formed. The result is illustrated in FIG. 9. As illustrated in FIG. 9, a border between the artificial lipid bilayer membrane (referred to as "bilayer membrane" in FIG. 9) and its peripheral cyclic bulk phase (referred to as "bulk phase" in FIG. 9) can be recognized. This shows that making the lipid solution thinner was completed.

Next, a cell membrane vesicle sampled from a bovine tracheal plain muscle was fused with the artificial lipid bilayer membrane, thereby inserting a K+ channel on the vesicle membrane into the artificial lipid bilayer membrane. By using the current measuring device, a current was measured with time.

Subsequently, only the $CaCl_2$ concentration of the aqueous solution with which the upper solution chamber 1 and the lower solution chamber 2 were filled was changed into 1 mM. Under this condition, a current was measured in the same manner.

Figure 10:
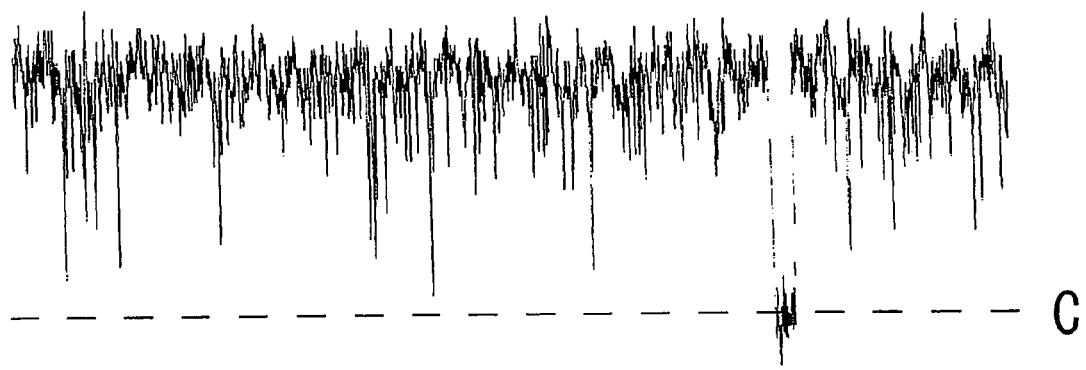
FIG. 10 illustrates a trace of a current in Example 1.
Figure 10:
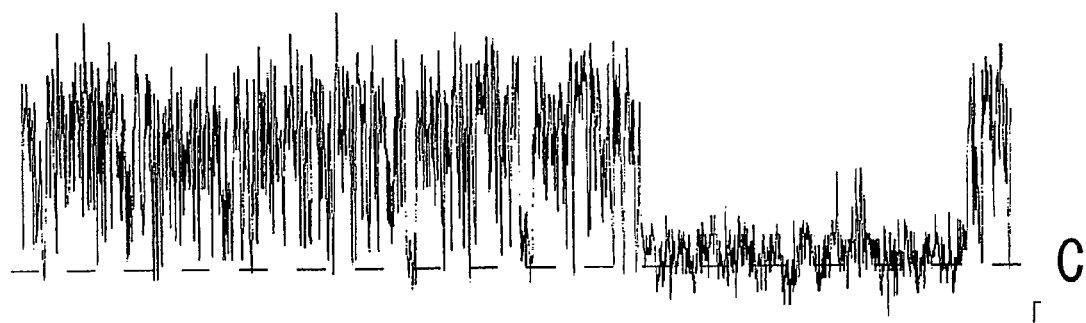
Figure 10:
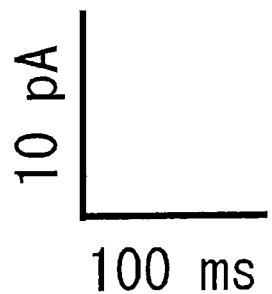
Figure 11:
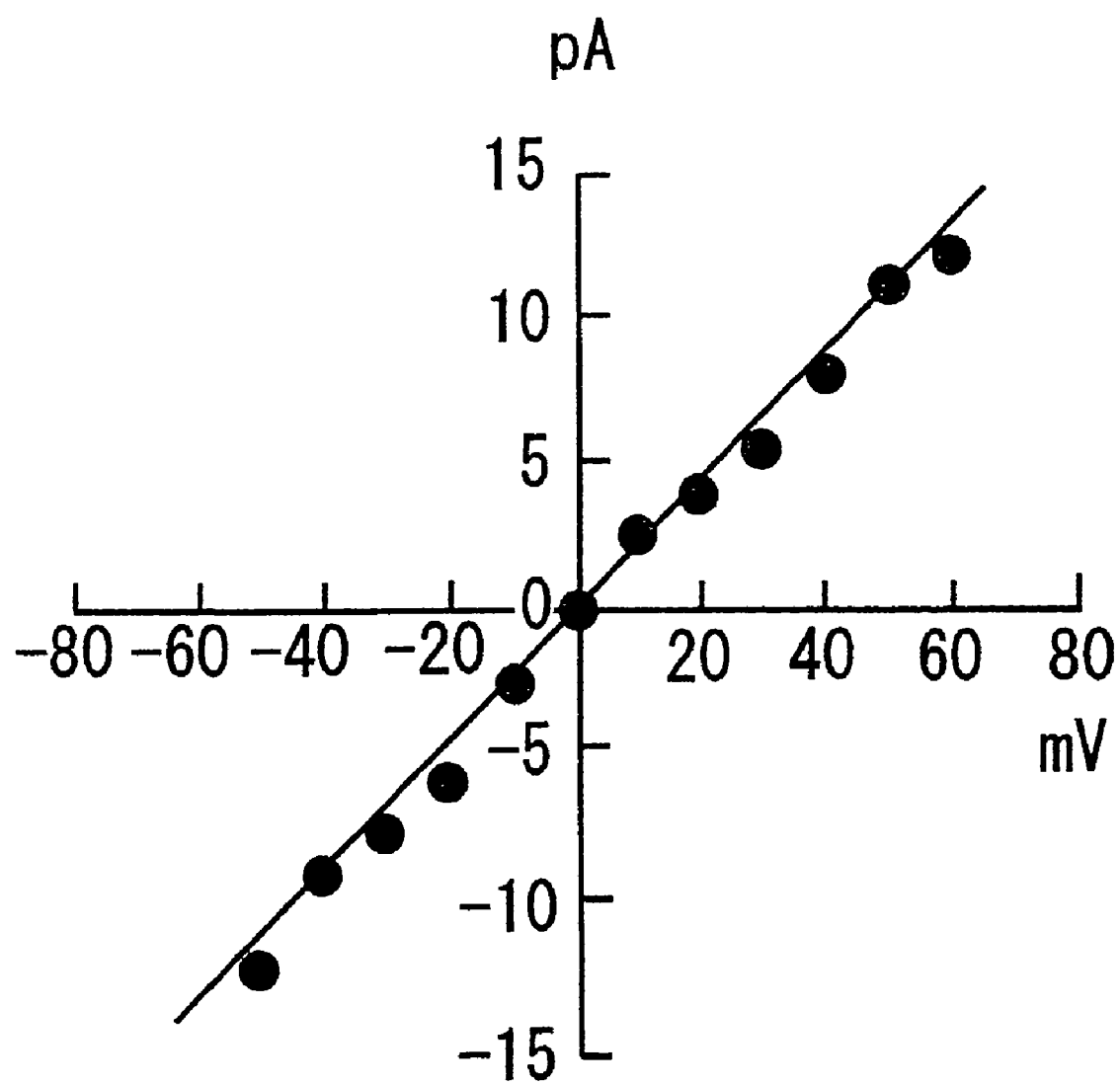
FIG. 11 illustrates a potential-current property in Example 1.
Figure 12:
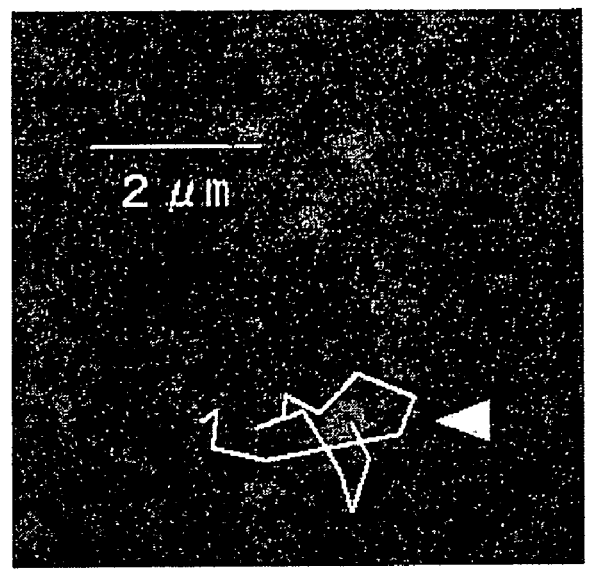
In FIG. 12, (a) illustrates a fluorescent image obtained by fluorescence-labeling alamethicin in Example 2. (b) illustrates a current trace obtained in Example 2.
Figure 12:
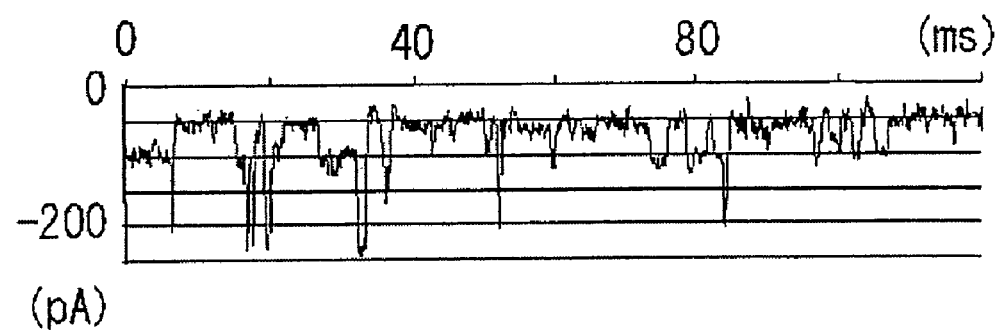
Figure 13:
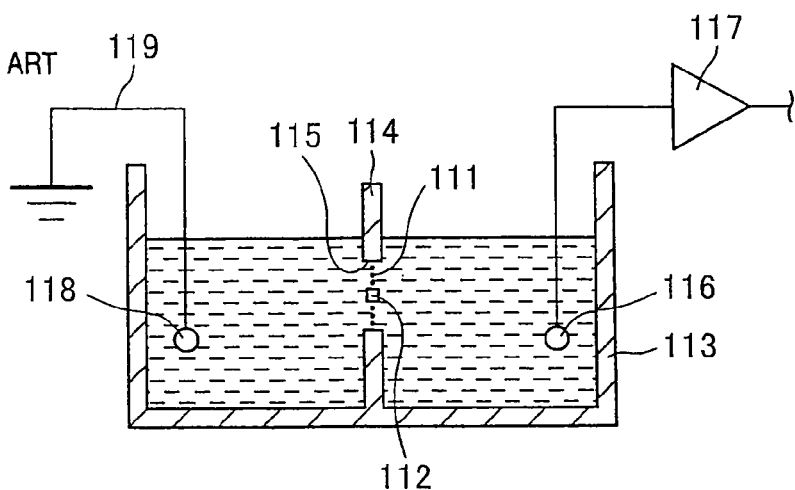
FIG. 13 is a schematic illustrating a conventional planar lipid bilayer method.
Figure 14:
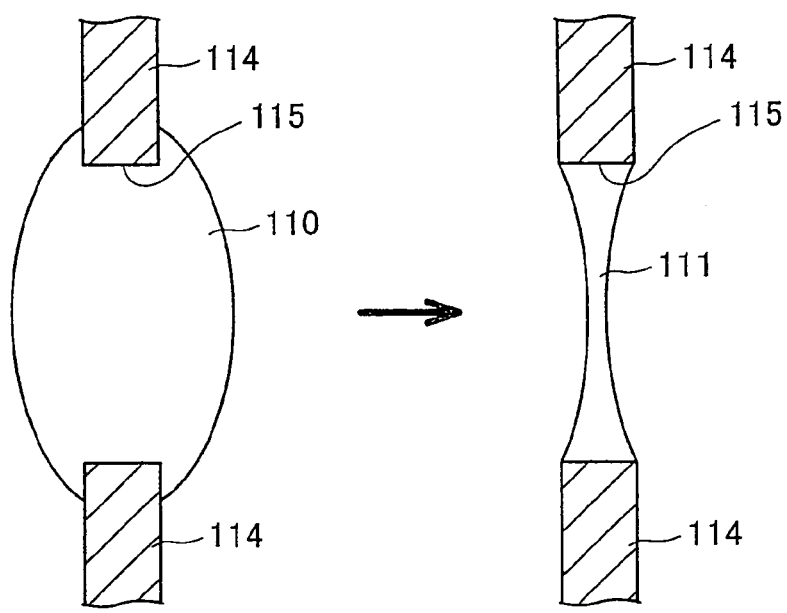
FIG. 14 illustrates a conventional vertical painting method.
Figure 15:
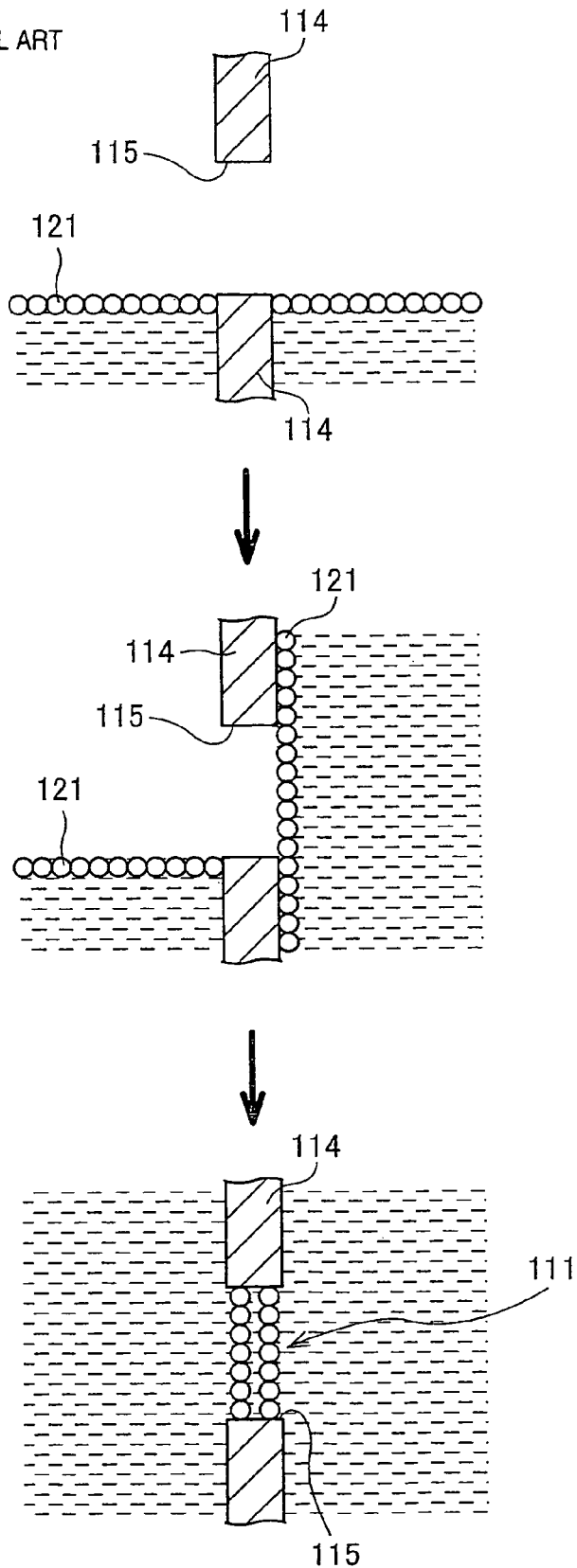
FIG. 15 illustrates a conventional vertical applying method.
Figure 16:
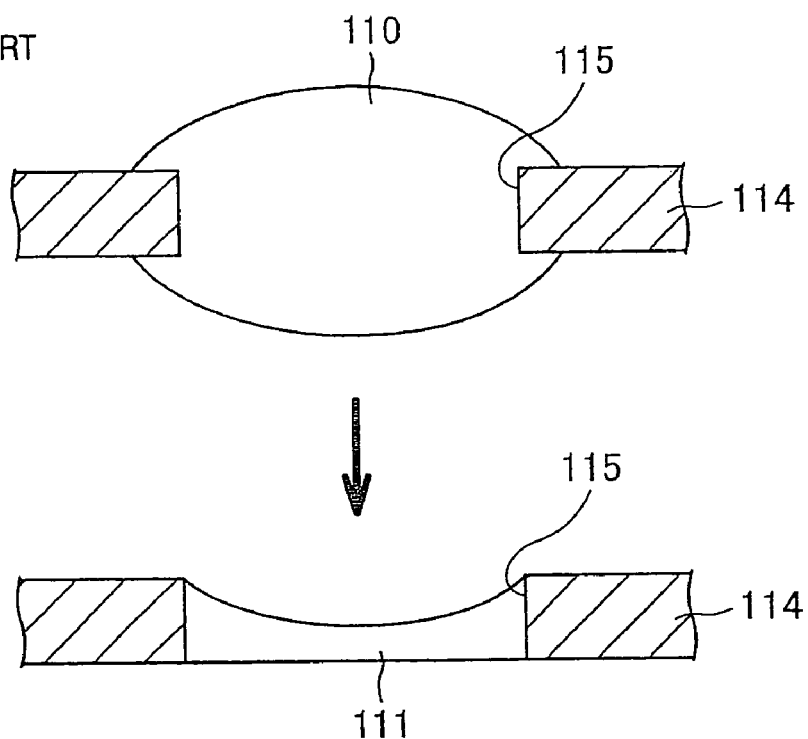
FIG. 16 illustrates a conventional horizontal artificial lipid bilayer membrane formation method.
Figure 16:
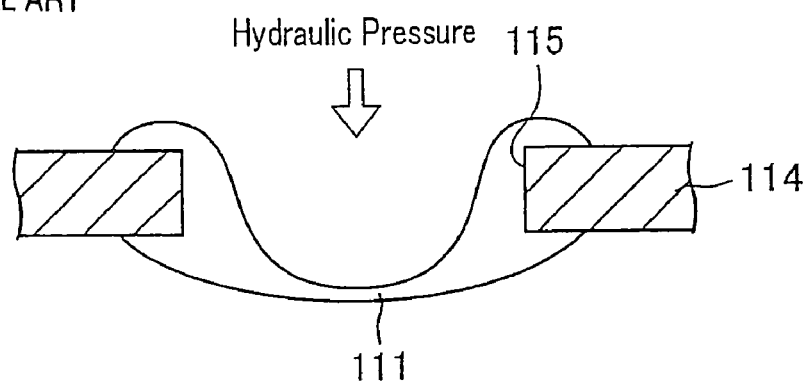
Figure 17:
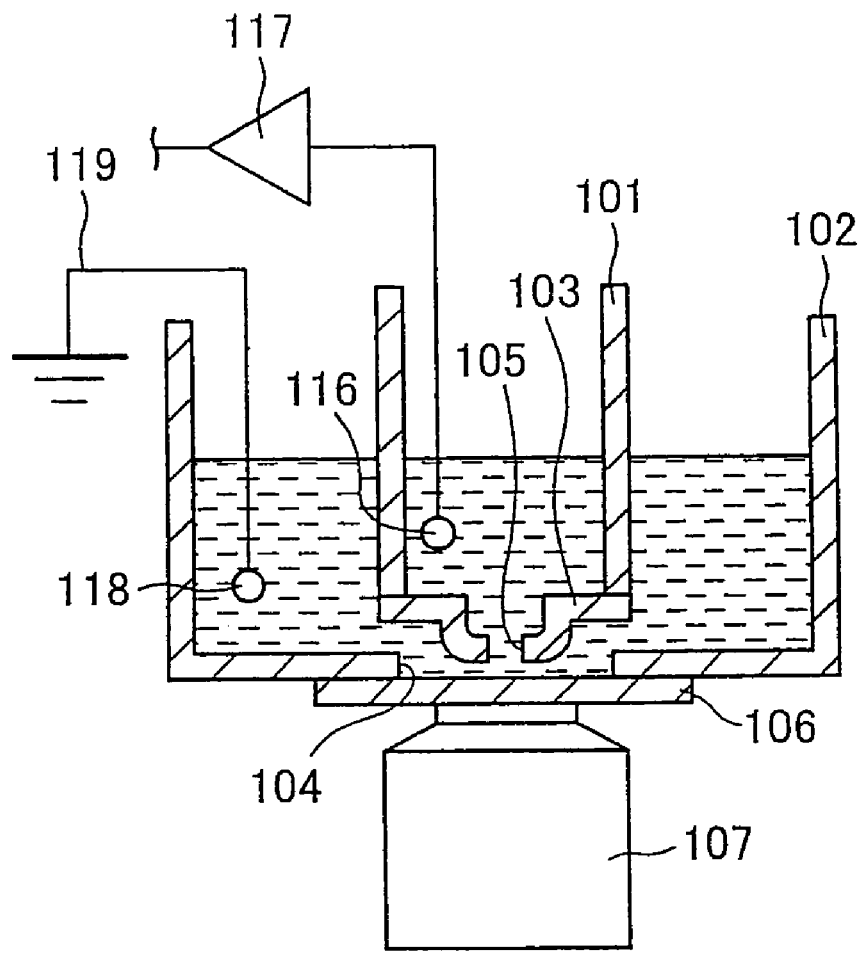
FIG. 17 illustrates a conventional current measuring device.
Figure 18:
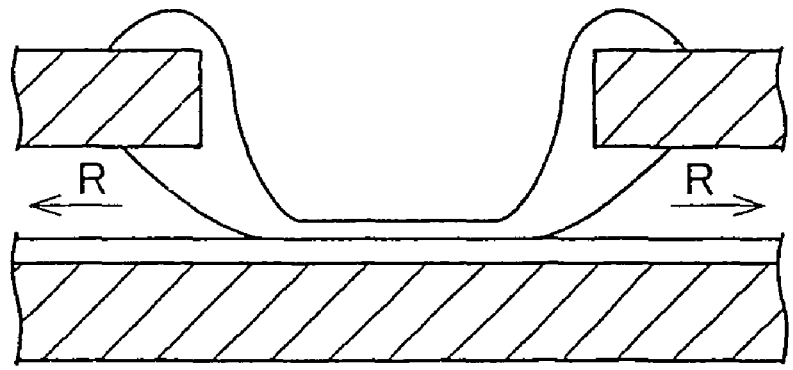
FIG. 18 illustrates an artificial lipid bilayer membrane formed on a conventional polymer gel layer.
Figure 18:
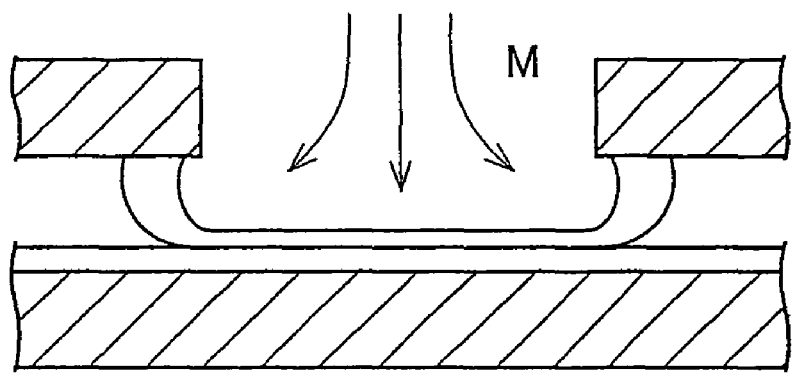
Figure 18:
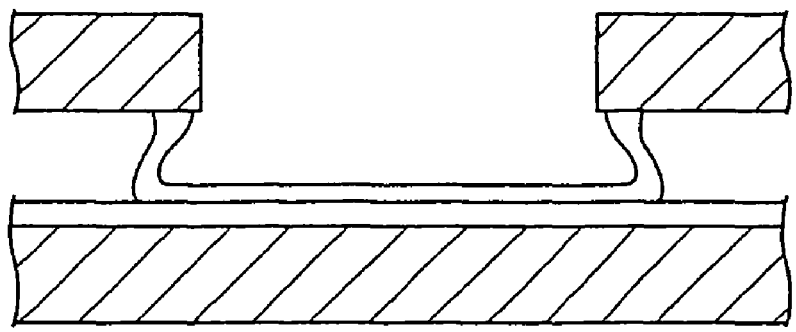

FIG. 10 illustrates the thus obtained trace of the current, and FIG. 11 illustrates a membrane potential-current property. FIG. 10(a) illustrates a trace of the current in case where the aqueous solution includes 100 mM KCl and $10^{-9}$ M $CaCl_2$, and FIG. 10(b) illustrates a trace of the current in case where the aqueous solution includes 100 mM KCl and 1 mM $CaCl_2$. It was confirmed that: when the concentration of $CaCl_2$ was $10^{-9}$ M, the ion channel was closed; and when the concentration of $CaCl_2$ was 1 mM, the ion channel is more likely to open. A pattern of the thus obtained trace of the current was the same as a pattern having been obtained as a result of a conventional experiment. This shows that: by using the current measuring device produced by using the artificial lipid bilayer membrane formation device of the present invention, it is possible to quickly and easily form a stable artificial lipid bilayer membrane, so that it is possible to obtain a reliable result of the current measurement. Further, FIG. 11 shows that a value of a single channel current (inductance of a single channel) was identical with a value obtained in a conventional method. This shows that: the current measuring device of the present invention can measure a current so that the agarose gel layer under the artificial lipid bilayer membrane has no influence on a channel property.

Example 2

Simultaneous Measurement of Formation of a Channel Pore (Optical Measurement) and a Single Channel Current Based on Antibiotic Alamethicin Instead of vesicle used in Example 1, a methanol solution of alamethicin (product of Sigma) fluorescence-labeled with Cy3 (product of Amensham Pharmacia) was added to the aqueous solution of the upper solution chamber 1 so that its final concentration was about $10^{-8}$ M. The fluorescence labeling of alamethicin was carried out as follows: glycine was added to a C end of alamethicin, and Cy3 was fixed on an amino group of glycine with a Cy3 mono functional dye kit (product of Amensham Pharmacia) so that glycine and Cy3 were combined with each other. Alamethicin is amphipathic peptide and moves from the liquid phase to the artificial lipid bilayer membrane in a natural manner so as to form an ion channel. Note that, as the aqueous solution with which the upper and lower solution chambers were filled, aqueous solution of 100 mM KCl and 10 mM Hepes (pH 7.4) was used.

By using the current measuring device of the present invention, the fluorescent image and an ion current based on alamethicin were simultaneously observed and measured. Note that, the fluorescent image was observed through a total internal reflection fluorescence microscope (TIRFM).

FIG. 12(a) illustrates the obtained fluorescent image of fluorescent alamethicin and a line indicative of Brownian motion in the membrane, and FIG. 12(b) illustrates a current trace. By using the current measuring device produced by using the artificial lipid bilayer membrane formation device of the present invention in this manner, it is possible to simultaneously carry out measurement of an ion current and optical observation of an ion channel.

Results of the foregoing Examples show that the lipid bilayer membrane formation device of the present invention can stably and quickly form the lipid bilayer membrane.

An artificial lipid bilayer membrane formation device according to the present invention includes: a membrane support whose plate portion has a membrane formation opening; and a membrane formation solution chamber which is capable of containing aqueous solution, the membrane formation solution chamber having a support layer for supporting an artificial lipid membrane, the artificial lipid bilayer membrane being formed on the membrane formation opening of the membrane support and being brought into contact with the support layer so as to be supported, and the artificial lipid bilayer membrane formation device is characterized by further including lipid solution exclusion means for excluding surplus lipid solution from lipid solution applied to the membrane formation opening without changing a hydraulic pressure, wherein: the membrane support is placed in the membrane formation solution chamber so that at least one side of the membrane formation opening is in contact with the aqueous solution, and the lipid solution is applied to the membrane formation opening, and the lipid solution is sandwiched by the aqueous solution and the support layer so as to be in contact with the support layer, and the lipid solution exclusion means excludes the surplus lipid solution under this condition so as to form a thinner artificial lipid bilayer membrane on the membrane formation opening.

Further, the artificial lipid bilayer membrane formation device according to the present invention includes: a membrane support whose plate portion has a membrane formation opening; and a membrane formation solution chamber which is capable of containing aqueous solution and storing the membrane support therein, and the artificial lipid bilayer membrane formation device further includes lipid solution exclusion means for excluding surplus lipid solution from lipid solution applied to the membrane formation opening by sucking the surplus lipid solution.

Further, it is more preferable to arrange the artificial lipid bilayer membrane formation device so that the membrane formation solution chamber includes a support layer for supporting the artificial lipid bilayer membrane formed on the membrane formation opening of the membrane support.

The membrane support is placed in the membrane formation solution chamber so that at least one side of the membrane formation opening is in contact with the aqueous solution, and the lipid solution is applied to the membrane formation opening, and the lipid solution is sandwiched by the aqueous solution and the support layer so as to be in contact with the support layer, and the lipid solution exclusion means excludes the surplus lipid solution under this condition so as to form a thinner artificial lipid bilayer membrane on the membrane formation opening.

According to the foregoing arrangement, the lipid solution exclusion means is provided, so that it is possible to exclude the surplus lipid solution from the lipid solution applied to the membrane formation opening without changing the hydraulic pressure. Thus, no pressure is exerted onto the membrane, so that the membrane is free from any breakage or any unstable condition in making the membrane thinner. Thus, it is possible to quickly form a stable and highly durable artificial lipid bilayer membrane.

The artificial lipid bilayer membrane formation device according to the present invention may be arranged so as to include an upper solution chamber, provided above the membrane formation solution chamber serving as a lower solution chamber, which is capable of containing aqueous solution, wherein the support layer is provided on a bottom of the lower solution chamber and the membrane support is a bottom of the upper solution chamber.

According to the foregoing arrangement, the upper solution chamber's bottom to which the lipid solution has been applied can be easily brought into contact with the support layer provided on the bottom of the lower solution chamber. Thus, it is possible to quickly and easily form a stable artificial lipid bilayer membrane with a simple arrangement.

Further, the artificial lipid bilayer membrane formation device according to the present invention may be arranged so that the lipid solution exclusion means is sucking means for causing a tubular member to suck the lipid solution applied to the membrane formation opening.

According to the foregoing arrangement, the sucking means is used to suck the surplus lipid solution from the lipid solution applied to the membrane formation opening. Therefore, it is possible to easily exclude the surplus lipid solution in short time, thereby making the artificial lipid bilayer membrane thinner.

Further, the artificial lipid solution membrane formation device according to the present invention may be arranged so that: the membrane support is movable in a direction in which the support layer provided on the membrane formation solution chamber is pressed, and the membrane support which is movable is used as the lipid solution exclusion means, and the lipid solution applied to the membrane formation opening is pressed against the support layer so that the lipid solution is extruded, so as to exclude the surplus lipid solution.

It is more preferable to arrange the artificial lipid bilayer membrane formation device according to the present invention so that: the membrane support is movable in a direction in which the membrane support presses the support layer provided on the membrane formation solution chamber, and the membrane support which is movable is used as the lipid solution exclusion means, and the membrane support applied to the membrane formation opening is pressed against the support layer, so as to divide the lipid solution into a portion on the membrane formation opening and a portion on an area other than the membrane formation opening.

According to the foregoing arrangement, the membrane support is movable, so that it is possible to exclude the surplus lipid solution by pressing the lipid solution against the support layer so that the lipid solution is extruded. Thus, it is not necessary to prepare a member for excluding the surplus lipid solution, so that it is possible to easily make the artificial lipid solution membrane thinner at low cost.

Further, in the artificial lipid bilayer membrane formation device according to the present invention, it is preferable that the support layer is made of polymer gel, and it is more preferable to use agarose or polyacrylamide as the polymer gel. The polymer gel may have any thickness. However, it is preferable that: in case where the lipid solution exclusion means is the sucking means, a thickness of the support layer made of the polymer gel is 100 nm or more and 2 mm or less, and in case where the lipid solution exclusion means is the membrane support which is movable, the thickness of the support layer made of the polymer gel is 0.5 mm or more and 2 mm or less. Further, it is preferable that the support layer made of the polymer gel has a higher area which is in contact with the membrane formation opening than other area, and it is more preferable that the higher area is higher than other area by 50 μm or more and 200 μm or less. According to the foregoing arrangement, the polymer gel layer supports the artificial lipid bilayer membrane so that the artificial lipid bilayer membrane is stable in upward and downward directions in making the membrane thinner.

Further, it is preferable to arrange the artificial lipid bilayer membrane formation device according to the present invention so that a diameter of the membrane formation opening is 10 μm or more and 500 μm or less.

According to the foregoing arrangement, it is possible to favorably form the artificial lipid bilayer membrane.

An artificial lipid bilayer membrane formation method according to the present invention includes the steps of: (i) applying lipid solution to a membrane formation opening provided in a plate portion of a membrane support so that at least one side of the membrane formation opening is in contact with aqueous solution; (ii) bringing the lipid solution applied to the membrane formation opening into contact with a support layer whose surface is hydrophilic by sandwiching the lipid solution between the aqueous solution and the support layer; and (iii) making an artificial lipid bilayer membrane thinner, formed on the membrane formation opening, by excluding surplus lipid solution from the lipid solution applied to the membrane formation opening without changing a hydraulic pressure.

According to the foregoing method, it is possible to exclude the surplus lipid solution from the lipid solution applied to the membrane formation opening without changing the hydraulic pressure. Thus, no pressure is exerted onto the membrane, so that the membrane is free from any breakage or any unstable condition in the step (iii). Thus, it is possible to quickly form a stable and highly durable artificial lipid bilayer membrane.

Further, the artificial lipid bilayer membrane formation method according to the present invention may be arranged so that: in the step (iii), a tubular member sucks the lipid solution so as to exclude surplus lipid solution.

According to the foregoing method, it is possible to easily exclude the surplus lipid solution in short time, so that it is possible to make the artificial lipid bilayer membrane thinner.

Further, the artificial lipid bilayer membrane formation method according to the present invention may be arranged so that: in the step (iii), the lipid solution applied to the membrane formation opening is pressed against the support layer so that the lipid solution is extruded so as to exclude the surplus lipid solution.

According to the foregoing arrangement, it is possible to easily make the artificial lipid bilayer membrane thinner at low cost.

An artificial lipid bilayer membrane according to the present invention is formed by using the aforementioned artificial lipid bilayer membrane formation method.

According to the foregoing arrangement, the artificial lipid bilayer membrane is formed by using the artificial lipid bilayer membrane formation method, so that the artificial lipid bilayer membrane has stability and high durability.

Further, the artificial lipid bilayer membrane according to the present invention may be arranged so that: a membrane protein is provided in the artificial lipid bilayer membrane, and the membrane protein may be an ion channel.

A current measuring device according to the present invention is produced by using the artificial lipid bilayer membrane formation device according to the present invention.

According to the foregoing arrangement, it is possible to use a stable artificial lipid bilayer membrane in measuring a current via the membrane, so that it is possible to measure a current with high accuracy.

Further, the current measuring device according to the present invention may be arranged so that the membrane formation solution chamber has a side face, having the support layer, which is made of a translucent material, and optical observation means for allowing observation of the artificial lipid bilayer membrane on the support layer is provided outside the side face.

According to the foregoing arrangement, it is possible to optically observe the artificial lipid bilayer membrane through the membrane formation solution chamber and the support layer.

Further, it is preferable to arrange the current measuring device according to the present invention so as to include: current measuring means electrically connected to the upper solution chamber; and earthing means electrically connected to the lower solution chamber.

Further, the current measuring device according to the present invention may be arranged so that: a membrane protein is provided in the artificial lipid bilayer membrane, and the membrane protein is an ion channel.

As described above, by using the artificial lipid bilayer membrane formation device of the present invention, it is possible to form a stable and highly durable artificial lipid bilayer membrane in short time. Further, the lipid bilayer membrane of the present invention which is formed by using the artificial lipid bilayer membrane formation device has stability and high durability.

When the current measuring device of the present invention is used, molecules provided in the stable artificial lipid bilayer membrane enable detection of various substances. In case where an ion channel is provided for example, it is possible to confirm a state of ion permeation. Therefore, the current measuring device can be used to analyze a function of the ion channel.

There are many kinds of ion channels, and the ion channels distribute in substantially all the cells. Thus, these ion channels are likely to cause any disease, so that many drugs targeting the ion channels are required. The present invention is usable in screening a drug targeting an ion channel and pharmacological test, and the usability is high.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

INDUSTRIAL APPLICABILITY

As described above, by using the lipid bilayer membrane formation device of the present invention, it is possible to form a stable and highly durable artificial lipid bilayer membrane in short time. Further, the lipid bilayer membrane of the present invention which is formed by using the lipid bilayer membrane formation device has stability and high durability. In addition, by using the current measuring device of the present invention, molecules provided in the stable artificial lipid bilayer membrane enable detection of various substances.

Thus, the present invention is widely applicable to: a bioscience field such as a biotechnology field, a medical field, and a pharmaceutical field, each of which uses a biological membrane model; an electronics field applying a biological membrane model as a certain device; and the like. For example, the present invention is applicable to: development of various kinds of sensors each of which uses a biological membrane model; screening and pharmacological test in developing a drug targeting a membrane protein; and the like.

The invention claimed is:

1. An artificial lipid bilayer membrane formation method, comprising the steps of:
    (i) applying a lipid solution to a membrane formation opening provided in a plate portion of a membrane support so that at least one side of the membrane formation opening is in contact with aqueous solution;
    (ii) bringing the lipid solution applied to the membrane formation opening into contact with a support layer whose surface is hydrophilic by sandwiching the lipid solution between the aqueous solution and the support layer without changing a hydraulic pressure of the aqueous solution; and
    (iii) making the artificial lipid bilayer membrane thinner, formed on the membrane formation opening, by excluding surplus lipid solution from the lipid solution applied to the membrane formation opening without changing the hydraulic pressure of the aqueous solution,
    the membrane support being a bottom of an upper solution chamber capable of containing the aqueous solution.

2. The artificial lipid bilayer membrane formation method as set forth in claim 1, wherein: in the step (iii), a tubular member sucks the lipid solution so as to exclude the surplus lipid solution.

3. The artificial lipid bilayer membrane formation method as set forth in claim 1, wherein: in the step (iii), the lipid solution applied to the membrane formation opening is pressed against the support layer so that the lipid solution is extruded so as to exclude the surplus lipid solution.

4. The artificial lipid bilayer membrane formation method as set forth in claim 1, wherein the support layer has a higher area in contact with the membrane formation opening than another area by 50 μm or more and 200 μm or less.

5. The artificial lipid bilayer membrane formation method as set forth in claim 1, wherein the membrane formation opening has a diameter of 10 μm or more and 500 μm or less, and the upper solution chamber has a volume of 0.01 cm$^3$ or more and 1.0 cm$^3$ or less.

* * * * *